(12) United States Patent
Gallant et al.

(10) Patent No.: US 7,243,386 B2
(45) Date of Patent: Jul. 17, 2007

(54) DOCKING STATION FOR PATIENT SUPPORT

(75) Inventors: Dennis J. Gallant, Harrison, OH (US); Dennis M. Lanci, Carlsbad, CA (US); John P. Biondo, Aurora, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 11/318,689

(22) Filed: Dec. 27, 2005

(65) Prior Publication Data

US 2006/0096028 A1 May 11, 2006

Related U.S. Application Data

(62) Division of application No. 10/150,574, filed on May 17, 2002, now Pat. No. 6,978,499.

(60) Provisional application No. 60/293,949, filed on May 25, 2001.

(51) Int. Cl.
*A61G 7/10* (2006.01)

(52) U.S. Cl. ............. 5/600; 5/611; 5/613; 5/620; 5/86.1

(58) Field of Classification Search .......... 5/600, 5/611, 613, 620, 86.1
See application file for complete search history.

(56) References Cited

U.S. PATENT DOCUMENTS

| | | | |
|---|---|---|---|
| 2,673,987 A | 4/1954 | Upshaw et al. | |
| 2,739,785 A | 3/1956 | Gray | |
| 2,834,030 A | 5/1958 | Jones | |
| 2,894,794 A | 7/1959 | Mays | |
| 3,167,789 A | 2/1965 | Wicks | |
| 3,241,850 A | 3/1966 | Propst | |
| 3,250,583 A | 5/1966 | Phillips | |
| 3,267,955 A | 8/1966 | Logan et al. | |
| 3,362,704 A | 1/1968 | Pitz | |
| 3,462,920 A | 8/1969 | Denny | |
| 3,514,794 A | 6/1970 | Pofferi | |
| 3,694,830 A * | 10/1972 | Koller | 5/610 |
| 3,769,502 A | 10/1973 | Schultz et al. | |
| 3,829,906 A | 8/1974 | McPhee | |
| 3,846,853 A * | 11/1974 | Jacobsson | 5/87.1 |
| 3,921,345 A | 11/1975 | Damico | |

(Continued)

FOREIGN PATENT DOCUMENTS

DE 570079 C 2/1933

(Continued)

OTHER PUBLICATIONS

Hill-Rom Future of Care 2.0 Videotape, date unknown; Copyright Hill-Rom Company, Inc.

(Continued)

*Primary Examiner*—Michael Trettel
(74) *Attorney, Agent, or Firm*—Barnes & Thornburg LLP

(57) ABSTRACT

According to the present disclosure, a transfer top adapted to carry a patient is transferable between a mobile base and a docking station in a hospital room. Thus, instead of transferring a patient between a stretcher and a hospital bed, the entire transfer top with the patient thereon is transferred between the mobile base and the docking station.

12 Claims, 12 Drawing Sheets

U.S. PATENT DOCUMENTS

| | | | |
|---|---|---|---|
| 4,072,157 A | 2/1978 | Wines, Jr. et al. | |
| 4,101,120 A | 7/1978 | Seshima | |
| 4,104,710 A | 8/1978 | Damico et al. | |
| 4,129,122 A | 12/1978 | Dout et al. | |
| 4,314,735 A | 2/1982 | Fullenkamp et al. | |
| 4,432,359 A | 2/1984 | James | |
| 4,475,322 A | 10/1984 | Russo et al. | |
| 4,592,104 A | 6/1986 | Foster et al. | |
| 4,612,679 A | 9/1986 | Mitchell | |
| 4,646,211 A | 2/1987 | Gallant et al. | |
| 4,753,055 A | 6/1988 | Durham, Jr. | |
| 4,811,435 A | 3/1989 | Foster et al. | |
| 4,821,470 A | 4/1989 | Kappers et al. | |
| 4,987,620 A * | 1/1991 | Sharon | 5/600 |
| 5,072,906 A | 12/1991 | Foster | |
| 5,077,843 A | 1/1992 | Foster et al. | |
| 5,097,550 A | 3/1992 | Marra, Jr. | |
| 5,107,636 A | 4/1992 | Schindele et al. | |
| 5,108,063 A | 4/1992 | Koerber, Sr. et al. | |
| 5,117,521 A | 6/1992 | Foster et al. | |
| 5,123,797 A | 6/1992 | Schnelle et al. | |
| 5,154,562 A | 10/1992 | Dornauer | |
| 5,174,285 A | 12/1992 | Fontenot | |
| 5,186,337 A | 2/1993 | Foster et al. | |
| 5,230,112 A | 7/1993 | Harrawood et al. | |
| 5,231,719 A | 8/1993 | Schnelle | |
| 5,247,962 A | 9/1993 | Walker | |
| 5,279,011 A | 1/1994 | Schnelle | |
| 5,284,255 A | 2/1994 | Foster et al. | |
| 5,299,338 A | 4/1994 | Foster | |
| 5,304,213 A | 4/1994 | Berke et al. | |
| 5,314,243 A | 5/1994 | McDonald et al. | |
| 5,315,726 A | 5/1994 | Borenstein | |
| 5,319,816 A | 6/1994 | Ruehl | |
| 5,335,651 A | 8/1994 | Foster et al. | |
| 5,337,845 A | 8/1994 | Foster et al. | |
| 5,370,111 A | 12/1994 | Reeder et al. | |
| 5,377,371 A | 1/1995 | Foster | |
| 5,396,673 A | 3/1995 | Foster | |
| 5,398,359 A | 3/1995 | Foster | |
| 5,452,807 A | 9/1995 | Foster et al. | |
| 5,455,975 A | 10/1995 | Foster | |
| 5,457,831 A | 10/1995 | Foster et al. | |
| 5,477,570 A * | 12/1995 | Hannant et al. | 5/86.1 |
| 5,497,766 A | 3/1996 | Foster et al. | |
| 5,507,734 A | 4/1996 | Everett, Jr. et al. | |
| 5,513,406 A | 5/1996 | Foster et al. | |
| 5,553,986 A | 9/1996 | Napierkowski et al. | |
| 5,555,582 A * | 9/1996 | Jerideau | 5/600 |
| 5,621,932 A | 4/1997 | Strachan | |
| 5,623,948 A | 4/1997 | VanMorris | |
| 5,651,150 A | 7/1997 | Kanitzer et al. | |
| 5,653,064 A | 8/1997 | Kappers et al. | |
| 5,878,536 A | 3/1999 | Demmitt et al. | |
| 5,966,760 A | 10/1999 | Gallant et al. | |
| 6,006,379 A | 12/1999 | Hensley | |
| 6,170,102 B1 | 1/2001 | Kreuzer | |
| 6,213,481 B1 | 4/2001 | Marchese et al. | |
| 6,272,702 B1 * | 8/2001 | Uchida et al. | 5/600 |
| 6,349,436 B1 | 2/2002 | Kreuzer | |
| 6,360,389 B1 | 3/2002 | Gallant et al. | |
| 6,526,609 B2 * | 3/2003 | Wong | 5/601 |
| 6,584,629 B2 * | 7/2003 | Tsuji et al. | 5/618 |
| 6,978,499 B2 | 12/2005 | Gallant et al. | |

FOREIGN PATENT DOCUMENTS

| | | |
|---|---|---|
| DE | 36236 C | 4/1952 |
| DE | 1930789 A | 12/1970 |
| DE | 2204573 A | 8/1973 |
| DE | 2228898 A | 1/1974 |
| DE | 2544221 A | 12/1976 |
| DE | 8434471 U | 5/1985 |
| DE | 3541017 A | 6/1986 |
| DE | 9204321 U | 5/1992 |
| DE | 4228873 C | 10/1993 |
| DE | 4416618 C | 7/1995 |
| DE | 4409069 A | 9/1995 |
| DE | 29720195 U | 1/1998 |
| DE | 19750476 A | 6/1999 |
| DE | 29923051 U | 4/2000 |
| DE | 200 18 317 U1 | 2/2001 |
| EP | 0 311 336 | 4/1989 |
| EP | 0 481 942 A1 | 4/1992 |
| EP | 0947187 A | 10/1999 |
| EP | 0 966 944 A2 | 12/1999 |
| EP | 0 969 241 A1 | 1/2000 |
| EP | 1030143 A | 8/2000 |
| FR | 2213070 A | 8/1974 |
| GB | 1 490 381 | 11/1977 |
| WO | WO 9420784 A | 9/1994 |
| WO | WO 98/33419 | 8/1998 |
| WO | WO 9850840 A | 11/1998 |
| WO | WO 0133529 A | 5/2001 |

OTHER PUBLICATIONS

Hill-Rom Future of Care Version 4.0 Videotape, 1999; Copyright Hill-Rom Company, Inc.

European Patent Office PCT International Search Report Dated Sep. 26, 2002. (7175-70583).

European Patent Office PCT International Search Report Dated Oct. 4, 2002. (7175-70584).

European Patent Office PCT International Search Report Dated Sep. 24, 2002. (7175-70585).

* cited by examiner

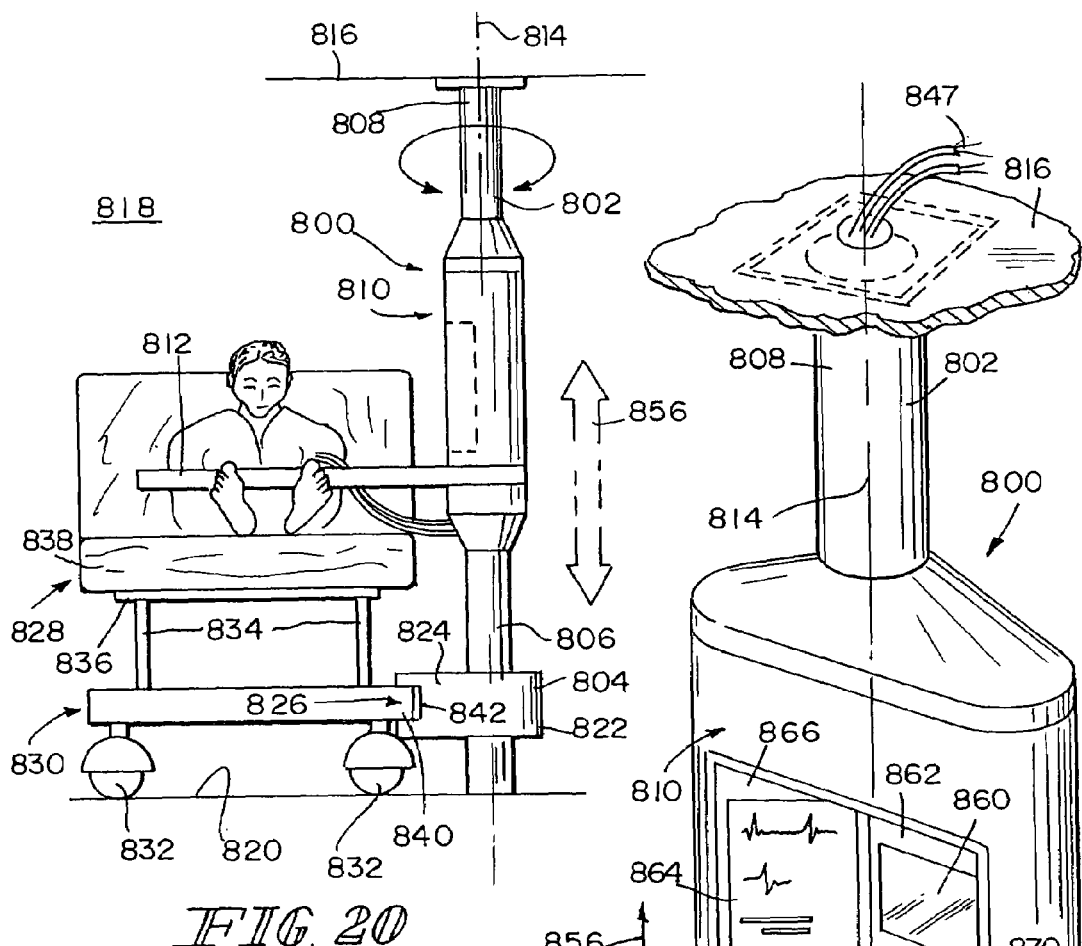
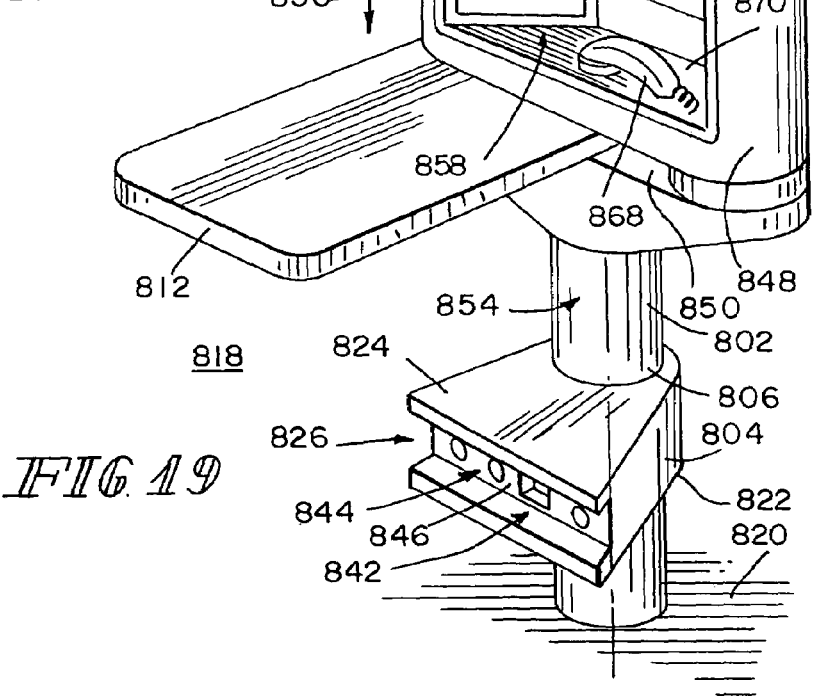
FIG. 20
FIG. 19

DOCKING STATION FOR PATIENT SUPPORT

This application is a divisional of U.S. patent application Ser. No. 10/150,574, which was filed May 17, 2002, which issued as U.S. Pat. No. 6,978,499 on Dec. 27, 2005, and which claimed priority under 35 U.S.C. § 119(e) to U.S. Provisional Patent Application Ser. No. 60/293,949, filed May 25, 2001; the disclosures of which are hereby incorporated herein by reference.

BACKGROUND AND SUMMARY OF THE INVENTION

Patients are oftentimes transported from location to location in a hospital or other healthcare facility on a stretcher that is highly mobile. Patients also spend a great deal of time during their stays in a hospital on a hospital bed located in a patient room. Hospital beds typically have various systems, such as drive and articulation mechanisms for raising, lowering and tilting a patient support deck, siderails with television, radio and other controls, patient weigh scales, and so on. Thus, hospital beds are usually less mobile than stretchers due to the increased weight of the hospital beds. It is sometimes difficult and time consuming to transfer patients between stretchers and hospital beds. On occasion, caregivers sustain back injuries while transferring patients. Thus, it is desirable in healthcare facilities to minimize the number of patient transfers between hospital beds and stretchers.

According to the present disclosure, a transfer top adapted to carry a patient is transferable between a mobile base and a stationary support structure (also referred to as a docking station or a patient care module). Thus, instead of transferring a patient between a hospital bed and a stretcher, the entire transfer top with the patient thereon is transferred between the mobile base and the stationary support structure.

An illustrative docking station includes a support rail extending away from a hospital room wall, and adapted to support a transfer top. In some embodiments, the docking station includes a pair of spaced-apart support rails and a pair of siderails. Each siderail is coupled to a respective support rail.

According to the present disclosure, an apparatus for use in a hospital comprises a wheeled base, a docking station coupled to a hospital room wall and a transfer top that is selectively couplable to the wheeled base to be transported with the wheeled base and to the docking station to be supported by the docking station.

In some embodiments, the illustrative apparatus includes a pair of support rails extending away from a hospital room wall, a bolster including portions coupled to the pair of support rails and configured to define a mattress-receiving space, and a patient support platform having a movable base and a mattress carried by the movable base. The patient support platform is movable to a position where the mattress is received in the mattress-receiving space.

According to the present disclosure, a patient care module comprises a pedestal and at least one support arm coupled to the pedestal and adapted to support a transfer top. The transfer top is transferable between the pedestal and a mobile platform. In some embodiments, the patient care module includes at least one service outlet coupled to the pedestal. In other embodiments, the patient care module includes an overbed table coupled to the pedestal and movable between a storage position extending in a perpendicular relation with the support arm and a use position extending in a parallel relation with the arm.

In some embodiments, the illustrative patient care module includes a base adapted to couple to a floor for rotation relative to the floor about an axis, a pedestal coupled to the base and a transfer top supported with respect to the pedestal. The pedestal and transfer top are configured to rotate with the base about the axis.

According to other embodiments, a patient care module comprises a pedestal, a plurality of patient monitoring modules coupled to the pedestal and a control panel coupled to the pedestal and configured to exchange data with the plurality of patient monitoring modules.

According to further embodiments, a patient care module comprises a pedestal, an overbed table coupled to the pedestal and a communication and control unit coupled to the pedestal.

An illustrative patient care module comprises a docking port having a coupler adapted to be coupled to a base frame of a hospital bed, a pedestal coupled to the docking port and at least one service outlet coupled to the pedestal.

An illustrative apparatus for use in a hospital comprises a wheeled base, a pedestal having a least one arm extending from a side of the pedestal in a cantilevered manner and a transfer top that is selectively couplable to the wheeled base to be transported with the wheeled base and to the at least one arm to be supported by the pedestal.

According to the present disclosure, a patient room comprises a bathroom area, a visitor area and a patient support apparatus. The patient support apparatus includes a head end, a foot end, a pedestal coupled to a floor and a transfer top supported with respect to the pedestal and configured to carry a patient. The patient support apparatus is rotatable about an axis between a first position having the foot end facing toward the bathroom area and a second position having the foot end facing toward the visitor area.

An illustrative patient room comprises a wall, a floor, a monitor coupled to the wall, a patient support apparatus including a floor-mounted pedestal, at least one patient monitoring module coupled to the pedestal and a service line transmitting data from the patient monitoring module to the monitor.

In some embodiments, a docking station comprises a column that rotates about a vertical axis and a docking port coupled to the column to rotate therewith and adapted to be coupled to a base frame of a hospital bed. In other embodiments, the docking station includes a communication-and-control unit coupled to the column above the docking port, and an overbed table coupled to the column above the docking port.

Additional features and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 19 is a perspective view of a column-mounted docking station, showing the column-mounted docking station including a vertical column, a docking port coupled to the column near a lower end of the column, a communication and control unit coupled to the column above the docking port, and an overbed table extending horizontally away from the communication and control unit, and FIG. 20 is an end elevation view of a hospital bed and the column-mounted docking station of FIG. 19, showing the hospital bed having a base frame member docked to the docking port so that services are provided to the bed through the column-mounted docking station, the communication and control unit and the overbed table being raisable and lowerable relative to the column as indicated by the vertical double-headed arrow, and the column-mounted docking station along with the hospital bed being rotatable about a vertical axis extending through the column.

DETAILED DESCRIPTION OF THE DRAWINGS

Throughout this description, (1) the terms "docking station," "pedestal" and "patient care module" are used interchangeably, (2) the terms "transfer base," "wheeled base," "mobile base," "stretcher base," "transport trolley" and "mobile platform" are used interchangeably, and (3) the terms "transfer top," "mattress support deck" and "patient support deck" are used interchangeably.

Figure 1:
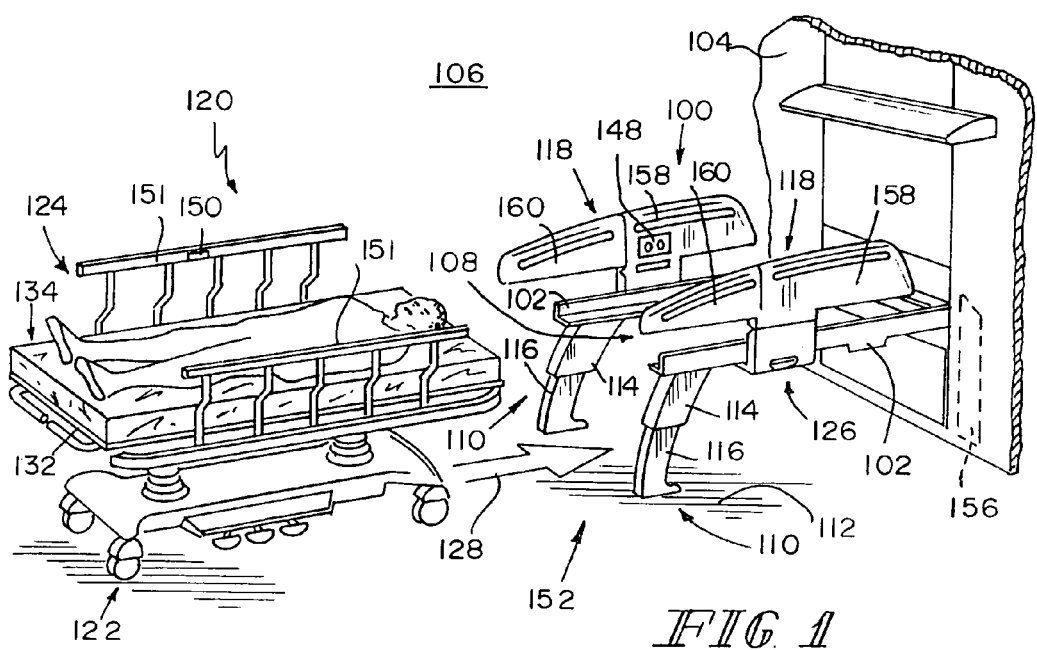
FIG. 1 is a perspective view of a stretcher and a docking station, showing the docking station including a pair of support rails extending horizontally away from a hospital room wall, the docking station including a pair of support legs coupled to ends of the support rails and extending downwardly therefrom to engage a floor of the hospital room, the docking station including a pair of siderails, each siderail extending upwardly from a respective support rail, a docking space being defined between the support rails, and the stretcher being arranged for movement in the direction of the arrow to deliver a transfer top of the stretcher into the docking space.

According to the present disclosure, a docking station 100 includes a pair of support rails 102 extending horizontally away from a wall 104 of a hospital room 106 in a cantilevered fashion as shown best in FIG. 1. The support rails 102 are spaced apart to define a docking space 108 between the support rails 102. A pair of support legs 110 are coupled to the outer or distal ends of the support rails 102 and extend downwardly therefrom to engage a floor 112 of the hospital room 106. Each leg 110 includes an upper portion 114 and a lower portion 116 that telescopes into and out of the upper portion 114. The docking station 100 also includes a pair of siderails 118. Each siderail 118 extends upwardly from a respective support rail 102 as shown, for example, in FIGS. 1-4.

A stretcher 120 includes a transfer base 122 and a transfer top 124 supported by transfer base 122 as shown in FIG. 1. The transfer base 122 and transfer top 124 are also referred to herein as the stretcher base and stretcher top. The transfer top 124 is detachable from the transfer base 122, and is attachable to a carrier or carriage 126 of the docking station 100. The carrier 126 is translatably mounted on the support rails 102 to move along the support rails 102 as will be described in further detail below. In the illustrative embodiments, the carrier 126 includes rollers or wheels which ride in tracks provided in the support rails 102. In alternative embodiments, the transfer top 124 is directly mounted on the support rails 102 to move along the support rails 102.

Figure 2:
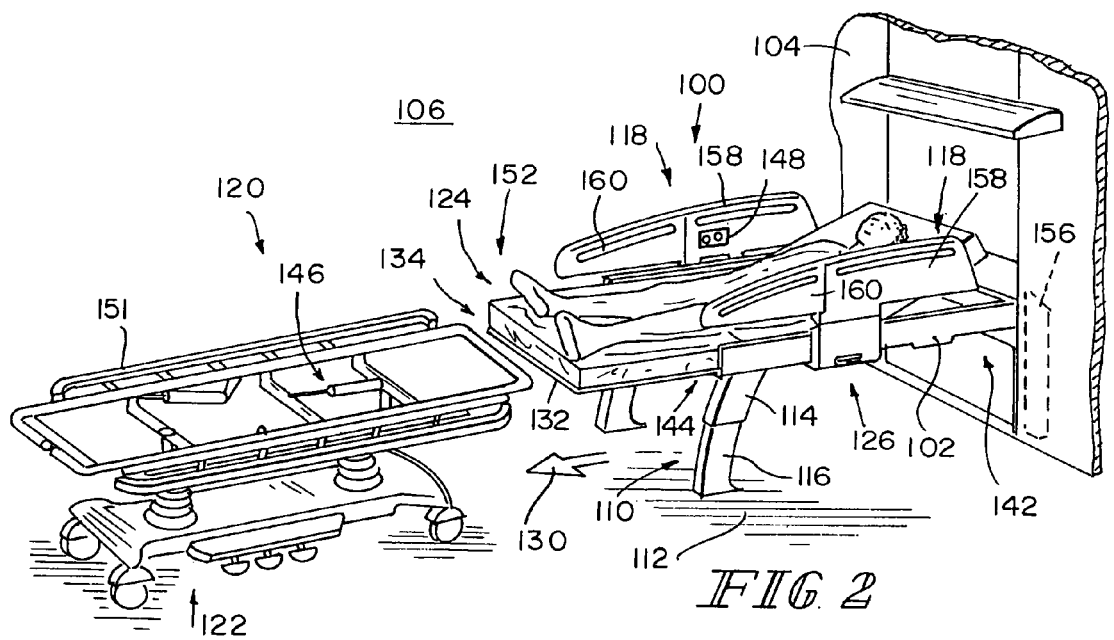
FIG. 2 is a perspective view similar to FIG. 1, showing the transfer top being decoupled from a transfer base of the stretcher, the transfer top being supported by the support rails and the support legs of the docking station, and the transfer base of the stretcher being moved in the direction of the arrow away from the docking station.
Figure 3:
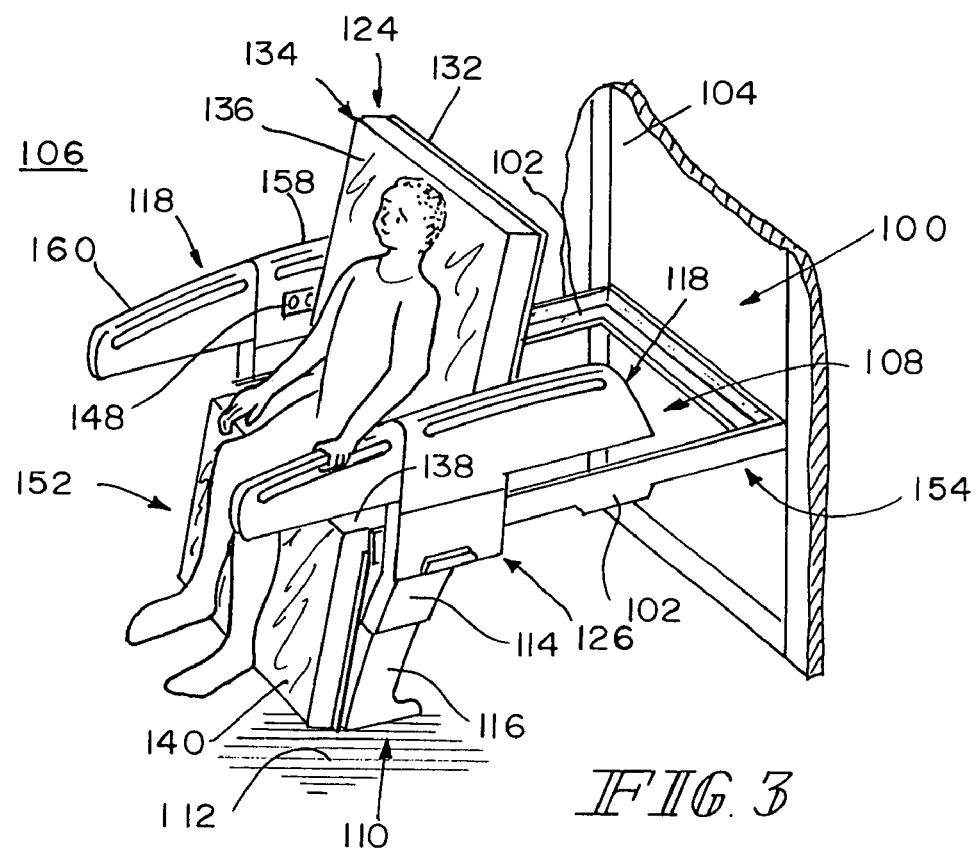
FIG. 3 is a perspective view similar to FIG. 2, showing the transfer top articulated to a chair position having a head section of the transfer top pivoted upwardly to a raised position, having a foot section of the transfer top pivoted downwardly to a lowered position, and having a seat section of the transfer top moved horizontally toward a foot end of the support rails along with the siderails.
Figure 4:
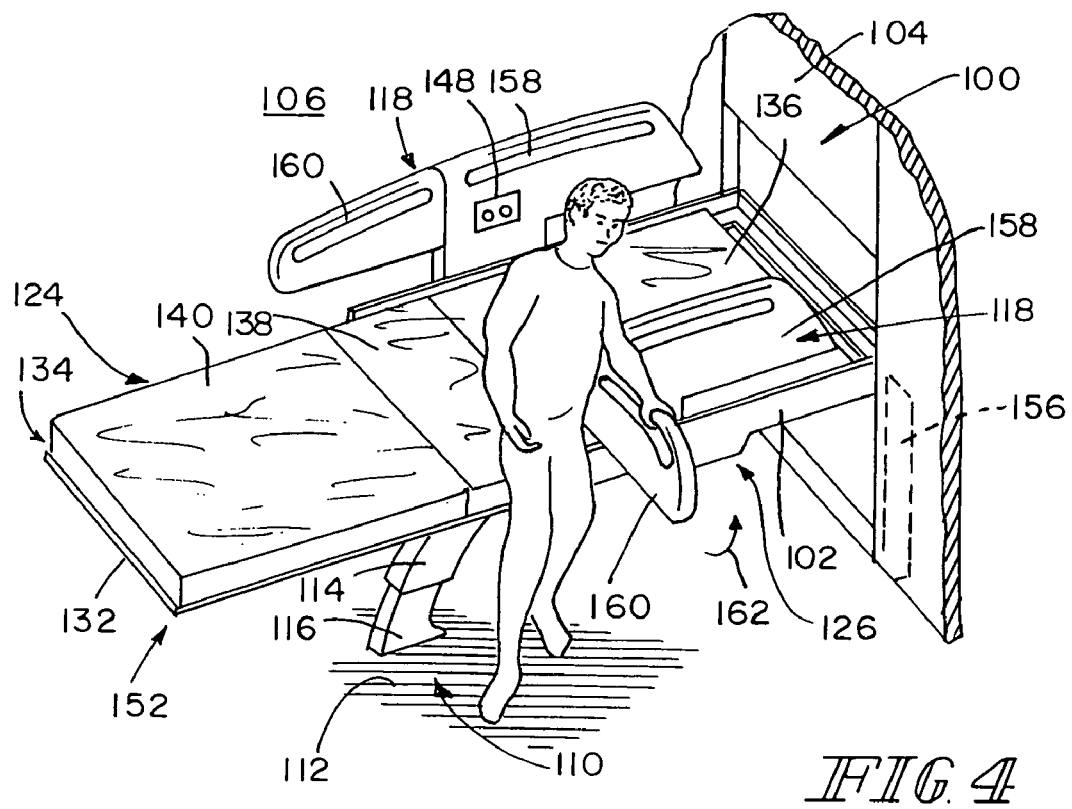
FIG. 4 is a perspective view similar to FIG. 2, showing the docking station including a motor package situated behind a wall panel, the transfer top and support rails being moved downwardly by the motor package in the direction of the vertical arrow to a lowered position, and a foot end section of one of the siderails being pivoted laterally outwardly about a vertical axis relative to a head end section of the associated siderail to allow patient egress from a side of the transfer top.

During transfer of the transfer top 124 from the transfer base 122 to the docking station 100, the stretcher 120 is moved in the direction of arrow 128, shown in FIG. 1, so that the transfer top 124 is received in the docking space 108. A first set of coupling mechanisms are operated to release the transfer top 124 from the transfer base 122 and a second set of coupling mechanisms are operated to couple the transfer top 124 to the carrier 126 supported by the support rails 102. Thereafter, the transfer base 122 is moved away from the docking station 100 in the direction of arrow 130, shown in FIG. 2, leaving the transfer top 124 in the docking space 108 supported by the support rails 102 as shown in FIGS. 2-4. The first and second sets of coupling mechanisms may include, for example, grippers that grip portions of the transfer top 124 or portions of the docking station 100, clutches that engage portions of the transfer top 124 or portions of the docking station 100, manually actuated pins that are received in apertures formed in the transfer top 124 or the docking station 100, solenoid actuated plungers that are received in apertures formed in the transfer top 124 or the docking station 100, hooks or latches that catch on posts or the like, blades that extend into and retract out of associated slots, or any other type of conventional mechanisms suitable to releasably couple the transfer top 124 to the carrier 126 and to the transfer base 122.

The transfer top 124 includes an articulated deck 132 and a mattress 134 supported by the deck 132. The deck 132 includes three sections and the mattress 134 includes associated portions that are supported by the three sections of the deck 132. Thus, the deck 132 cooperates with the mattress 134 to provide the transfer top 124 with a head section 136, a seat section 138, and a foot section 140 as shown in FIG. 3. The docking station 100 includes drive mechanisms 142 that automatically couple with articulation mechanisms 144 included in the transfer top 124 when the transfer top 124 is coupled to the support rails 102 as shown in FIG. 2. Likewise, the stretcher 120 also includes drive mechanisms 146 that interact with the articulation mechanisms 144 of the transfer top 124 when the transfer top 124 is coupled to the stretcher 120.

Siderails 118 include controls 148 for inputting patient and/or caregiver commands that control the drive mechanisms 142 of the docking station 100. Commands from the controls 148 on the siderails 118 actuate the drive mechanisms 142 included in the docking station 100 which act through the articulation mechanisms 144 included in the transfer top 124 to move the sections 136, 138, 140 relative to the support rails 102 when the transfer top 124 is coupled to the docking station 100. The seat section 138 of transfer top 124 is coupled to the carrier 126 supported on the support rails 102. In addition, the siderails 118 are coupled to the carrier 126. Thus, the siderails 118 and the transfer top 124 move with the carrier 126 as the carrier 126 moves along the support rails 102. As shown in FIG. 1, the stretcher 120 also includes controls 150 mounted on stretcher siderails 151 that are used to control the drive mechanisms 146 of the stretcher 120. Thus, the transfer top 124 is articulatable to a variety of positions when coupled to the docking station 100 and when coupled to the stretcher 120.

Illustrative transfer top 124 is moveable between a horizontal position, shown in FIG. 2, having the upper surfaces of the mattress portions corresponding to the head, seat, and foot sections 136, 138, 140 in substantially coplanar horizontal relationship with one another and a chair position, shown in FIG. 3, having the head section 136 pivoted upwardly relative to the seat section 138 to a raised position and having the foot section 140 pivoted downwardly relative to the seat section 138 to a lowered position. During movement of the transfer top 124 into the chair position shown in FIG. 3, the carrier 126, the seat section 138 along with the rest of the transfer top 124, and the siderails 118 all move horizontally toward a foot end 152 of the support rails 102. The docking station 100, therefore, includes a driver 154 shown in FIG. 3 that moves the carrier 126 along the support rails 102 toward the foot end 152 of the support rails 102 during articulation of the transfer top 124 to the chair position. Movement of the carrier 126 toward the foot end 152 of the support rails 102 facilitates patient egress from the transfer top 124.

It is well known in the hospital bed art that drive motors with various types of transmission elements including lead screw drives and various types of mechanical linkages may be used to cause relative movement of portions of hospital beds, stretchers, chairs and other types of patient transport and support apparatuses (sometimes collectively referred to herein as "patient support apparatuses"). As a result, terms such as "drive mechanism," "drive assembly," "drive," and "driver" are intended to cover all types of electrical, mechanical, electromechanical, hydraulic and pneumatic drive systems that are operable to move portions of a patient support apparatus relative to other portions of the patient support apparatus. In addition, terms such as "articulation mechanism," "linkage assembly," "linkage," and "transmission assembly" are intended to cover all types of components such as belts, gears, racks, pinions, interconnected links, torque converters, ball screws, chains, sprockets, pulleys, cables, and the like, as well as combinations of these, that couple to drive mechanism and that are configured to transfer motion from the drive mechanism to a portion of a patient support apparatus. Reference may be made to U.S. Pat. No. 6,006,379, which is hereby incorporated by reference herein, and which is entitled "Articulating Bed Frame," for examples of illustrative drive and articulation mechanisms.

The docking station 100 includes a motor package 156 (in phantom) situated behind the room wall 104. The motor package 156 includes a driver that couples to the support rails 102 via a linkage assembly. The driver of the motor package 156 is operable to move the support rails 102 vertically between a raised position, shown in FIGS. 1-3, and a lowered position, shown in FIG. 4. The siderail-mounted controls 148 command the operation of the driver of the motor package 156. When the support rails 102 are in the lowered position, the transfer top 124 is supported at a position close to the floor 112 allowing the patient to egress from a side of the transfer top 124 more easily than when the support rails 102 are at the raised position. The siderail 118 includes a head-end section 158 and a foot-end section 160 that pivots laterally outwardly about a vertical axis in the direction of arrow 162 relative to the head-end section 158 to facilitate patient egress from the transfer top 124 as shown in FIG. 4. Optionally, the siderails 118 may be equipped with interlock mechanisms that operate to lock sections 158, 160 of the siderail 118 together until the support rails 102 are moved to the lowered position.

Figure 5:
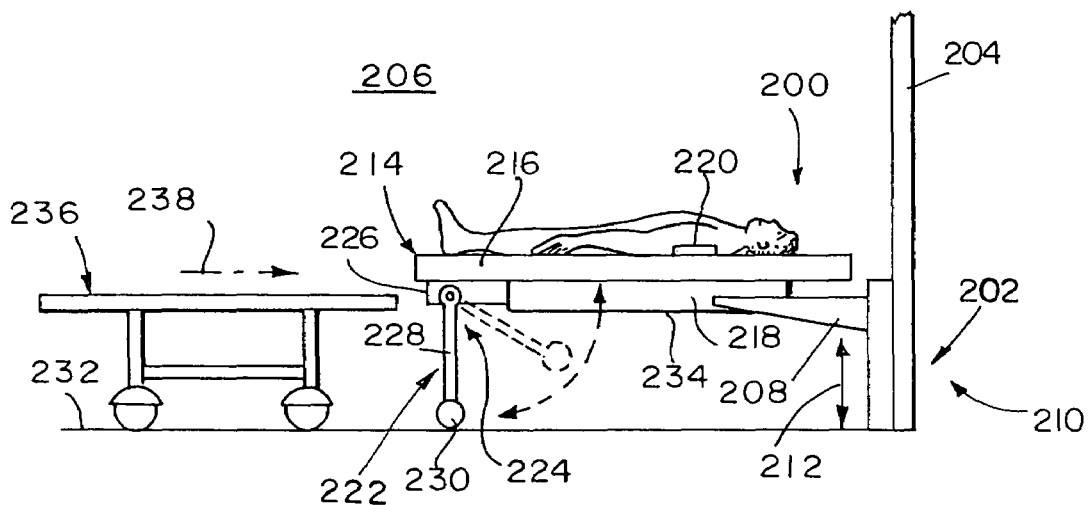
FIG. 5 is a side elevation view of a first alternative docking station, showing the first alternative docking station including a lift mechanism and a lift arm extending horizontally in a cantilevered fashion from the lift mechanism, the lift mechanism being operable to raise and lower the lift arm as indicated by the vertical double-headed arrow, a transfer top including a mattress and a mattress support deck beneath the mattress, the mattress support deck being coupled to the lift arm to raise and lower therewith, the transfer top including a retractable leg that pivots relative to the mattress support deck between a use position extending vertically downwardly from the mattress support deck to engage a floor and a storage position extending horizontally adjacent an undersurface of the mattress support deck, and a transport trolley arranged to be moved in the direction of the horizontal arrow to a position beneath the transfer top so that the transfer top can be decoupled from the first alternative docking station and transported away from the first alternative docking station by the transport trolley.

Referring now to FIG. 5, a first alternative docking station 200 includes a lift mechanism 202 coupled to a wall 204 of a hospital room 206 and a pair of spaced-apart lift arms 208 extending horizontally in a cantilevered fashion away from the lift mechanism 202. The lift mechanism 202 includes drive mechanisms 210 that are operable to raise and lower the lift arms 208 as indicated in FIG. 5 by a vertical double-headed arrow 212. A transfer top 214 includes a mattress 216 and a mattress support deck 218 beneath the mattress 216. The mattress support deck 218 includes one or more receptacles (obscured view) that are adapted to receive the lift arms 208 to couple the transfer top 214 to the docking station 200. The transfer top 214 raises and lowers with the lift arms 208. The docking station 200 includes a suitable controller 220, such as a wall-mounted, pendant or wireless controller, that receives user inputs to command the operation of the lift mechanism 202 to control the elevation of the lift arms 208 and the transfer top 214.

The transfer top 214 includes a leg assembly 222 having one or more coupling members 224 that are received in corresponding receptacles formed in a foot-end portion 226 of the mattress support deck 218, and having one or more retractable legs 228 that are pivotably coupled to the distal ends of the respective coupling members 224 for pivoting movement about a horizontal axis 229 that extends in a transverse direction relative to the transfer top 214 as shown in FIG. 5. The retractable legs 228 pivot relative to the mattress support deck 218 between a use position extending vertically downwardly from the mattress support deck 218 so that wheels 230 coupled to the distal ends of the respective legs 228 engage a floor 232 of the hospital room 206 and a storage position extending horizontally adjacent an undersurface 234 of the mattress support deck 218.

The transfer top 214 is detachable from the lift arms 208 and is attachable to a transport trolley 236. Suitable locking mechanisms (obscured view) are provided for coupling the transfer top 214 to the lift arms 208 and to the transport trolley 236. When the trolley 236 moves in the direction of a horizontal arrow 238 from a first position spaced apart from the transfer top 214 into a second position located beneath the transfer top 214, the transport trolley 236 engages the retractable legs 228 and automatically pivots the legs 228 from their respective use positions to their respective storage positions. After the transfer trolley 236 is in the second position, the transfer top 214 is decoupled from the lift arms 208 of the docking station 200 and is coupled to the transport trolley 236 for transport away from the docking station 200.

Figure 6:
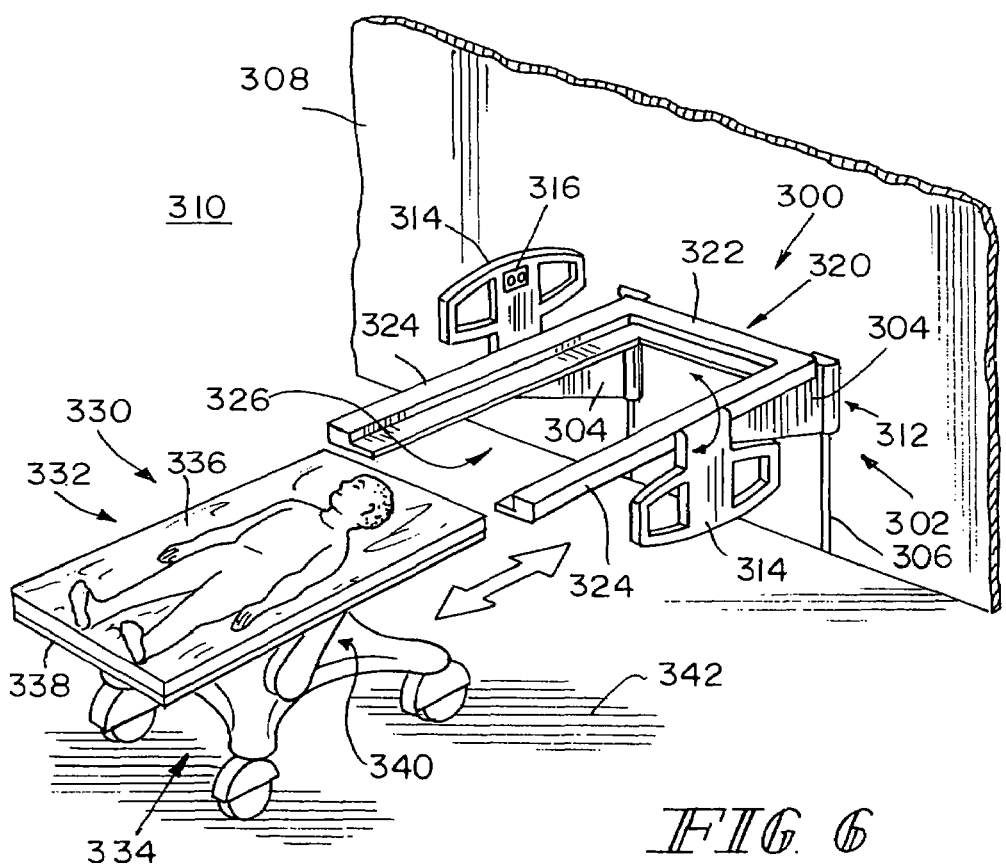
FIG. 6 is a perspective view of a second alternative docking station, showing the second alternative docking station including a pair of lift arms extending horizontally in a cantilevered fashion away from a wall of a hospital room, the second alternative docking station including a bolster assembly coupled to the pair of lift arms, the bolster assembly including a head end portion extending horizontally adjacent to the hospital room wall, the bolster assembly including a pair of side portions extending horizontally away from the head end portion, the bolster assembly being formed to include a mattress-receiving space between the pair of side portions, a mobile platform being arranged for docking to the second alternative docking station so that a mattress of the mobile platform is received in the mattress-receiving space, and the bolster assembly having an upper surface that cooperates with an upper surface of the mattress to increase the amount of surface area available to support the patient when the mobile platform is docked to the second alternative docking station.

According to the present disclosure, a second alternative docking station 300 includes a lift mechanism 302 and a pair of spaced-apart lift arms 304 extending horizontally in a cantilevered fashion away from the lift mechanism 302 through associated slots 306 formed in a wall 308 of a hospital room 310 as shown in FIG. 6. The lift mechanism 302 is positioned to lie behind the hospital room wall 308. In addition, the lift mechanism 302 includes drive mechanisms 312 that operate to raise and lower the lift arms 304. The docking station 300 includes a pair of siderails 314 having controls 316 that are used to operate the lift mechanism 302.

Figure 7:
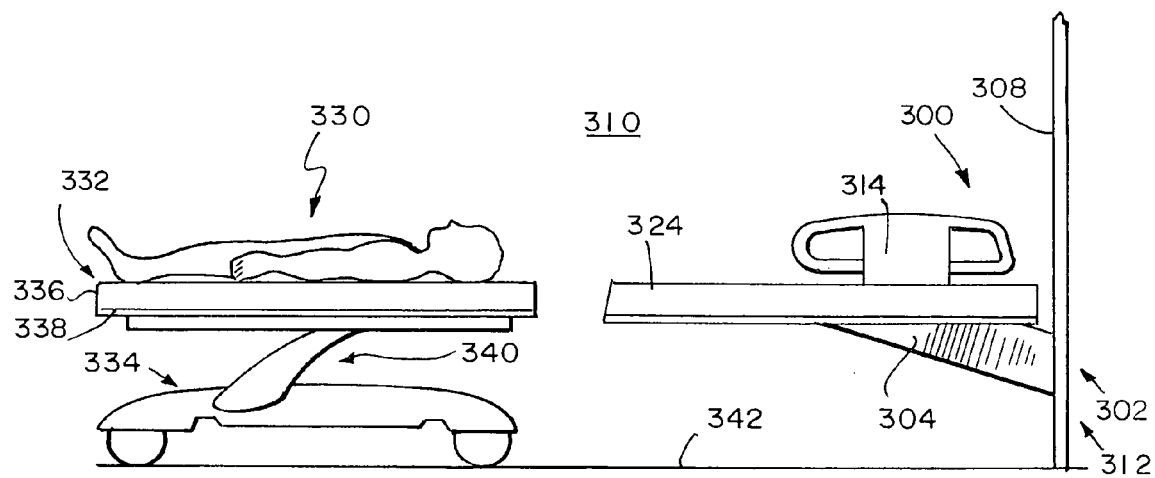
FIG. 7 is a side elevation view of the second alternative docking station and the mobile platform of FIG. 6, showing the mobile platform being spaced apart from the second alternative docking station.
Figure 8:
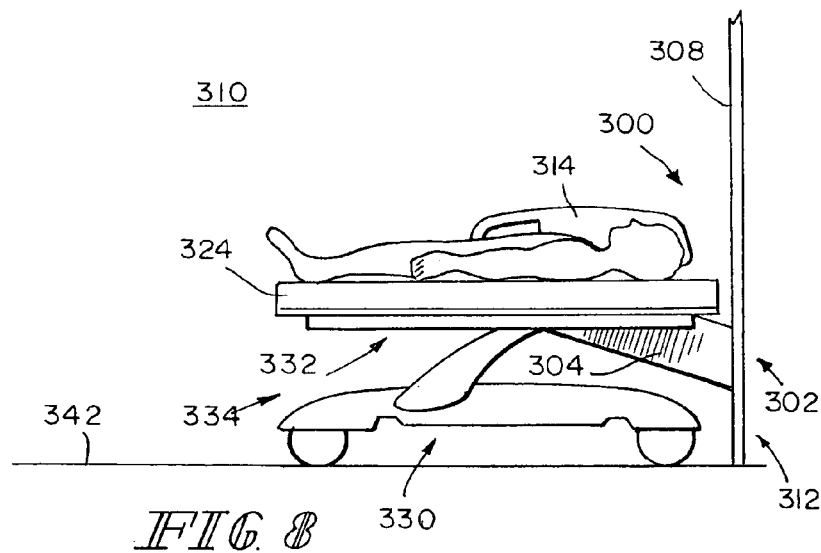
FIG. 8 is a side elevation view similar to FIG. 7, showing the mobile platform docked to the second alternative docking station.

The docking station 300 includes a bolster assembly 320 (also referred to as a bolster) coupled to the pair of lift arms 304 as shown in FIGS. 6-8. The bolster assembly 320 includes a head end portion 322 extending horizontally between the lift arms 304 adjacent to the room wall 308. The bolster assembly 320 also includes a pair of side portions 324 extending horizontally away from the head end portion 322 in parallel relation with the lift arms 304. Thus, the bolster assembly 320 is formed to include a mattress-receiving space 326 between the pair of side portions 324. In some embodiments, the head end and side portions 322, 324 of the bolster assembly 320 include patient support elements, such as one or more air bladders or one or more foam pads, and an outer cover that encases the patient support elements. Each of the siderails 314 is coupled to a respective side portion 324 of the bolster assembly 320 for pivoting movement about a longitudinal-extending axis between a raised position and a lowered position.

A mobile platform 330 includes a transfer top 332 and a wheeled frame 334 that carries the transfer top 332 as shown best in FIGS. 6-8. The transfer top 332 includes a mattress 336 and a mattress support deck 338 beneath the mattress 336. The mobile platform 330 is configured to dock to the docking station 300. However, unlike the docking stations 100, 200 in which the stretcher base 122 and the transport trolley 236 are moved away from the docking stations 100, 200, respectively, after the associated transfer tops 124, 214 are attached to the support rails 102 and the lift arms 208, respectively, the wheeled frame 334 of the mobile platform 330 remains underneath the transfer top 332 when the mobile platform 330 is docked to the docking station 300.

When the mobile platform 330 is docked to the docking station 300, the mattress 336 is received in the mattress-receiving space 326 having upper surfaces of the head end and side portions 322, 324 of the bolster assembly 320 substantially in coplanar relation with the upper surface of the mattress 336. Thus, the bolster assembly 320 cooperates with the mattress 336 to increase the amount of surface area available to support the patient when the mobile platform 330 is docked to the docking station 300. The wheeled frame 334 includes drive mechanisms 340 that are operable to change the elevation of the mattress 336 relative to the floor 342 of the hospital room 310. When the mobile platform 330 is docked to the docking station 300, the operation of the drive mechanisms 312 of the lift mechanism 302 of the docking station 300 is coordinated with the operation of the drive mechanisms 340 of the wheeled frame 334 of the mobile platform 330 so that the mattress 336 and the bolster assembly 320 raise and lower together.

Figure 9:
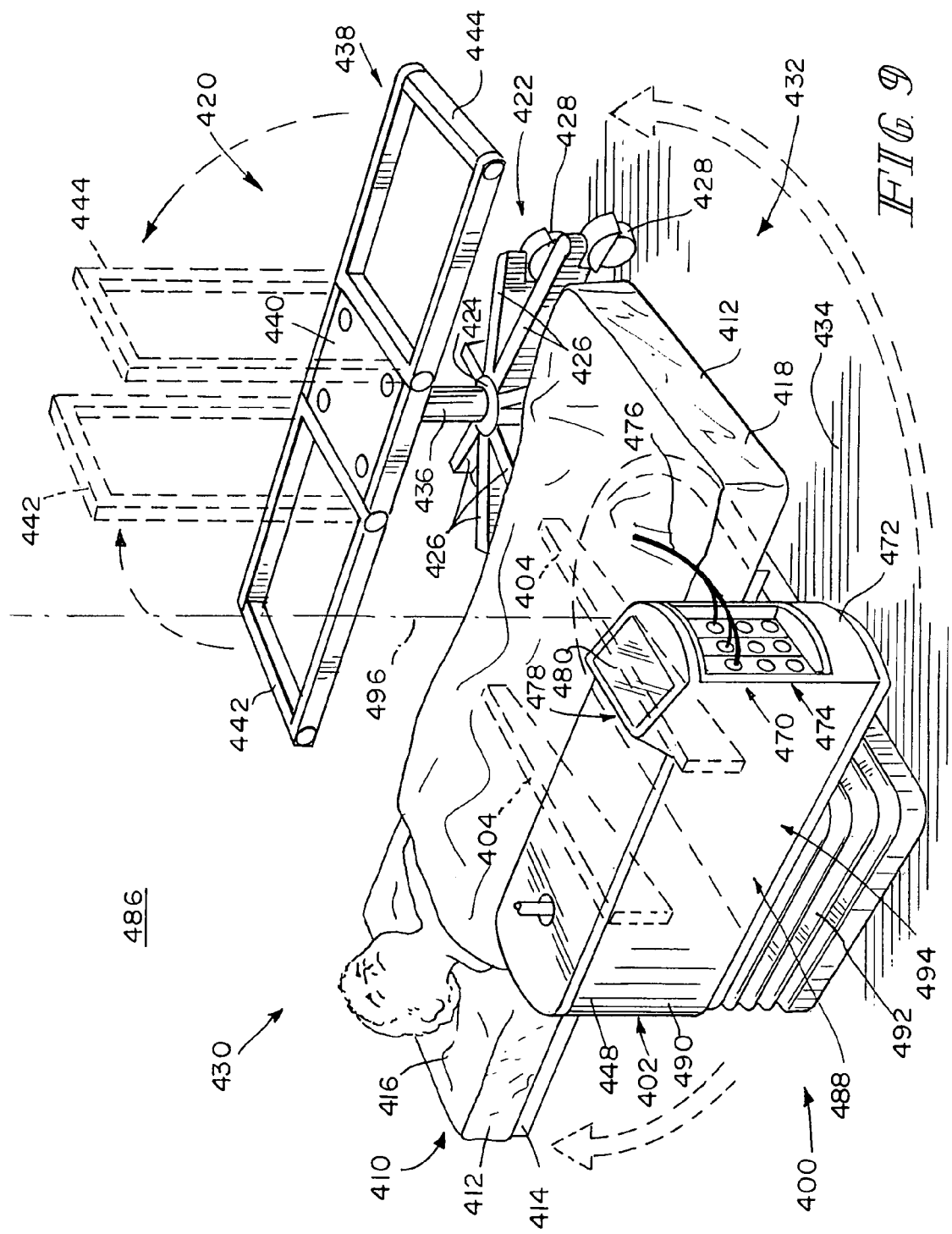
FIG. 9 is a perspective view of a floor-mounted patient care module, a transfer top and a wheeled transport base, showing the patient care module including a pedestal and a pair of lift arms (in phantom) extending horizontally from the pedestal, the patient care module including a base panel extending from a bottom of the pedestal beneath the lift arms, the transfer top being supported above the base panel by the lift arms, the base panel along with the rest of the patient care module and the transfer top being pivotable about a vertical axis that is offset from the pedestal, the transport base including a lower frame having a central hub and six spokes radiating substantially horizontally outwardly from the central hub, the transport base including casters coupled to distal ends of the spokes, the transport base including a vertical column extending upwardly from the central hub and a mattress support deck coupled to an upper end of the vertical column, and the mattress support deck including a center section and a pair of end sections that are coupled to the center section for pivoting movement between horizontal positions (in solid) and vertical positions (in phantom)
Figure 11:
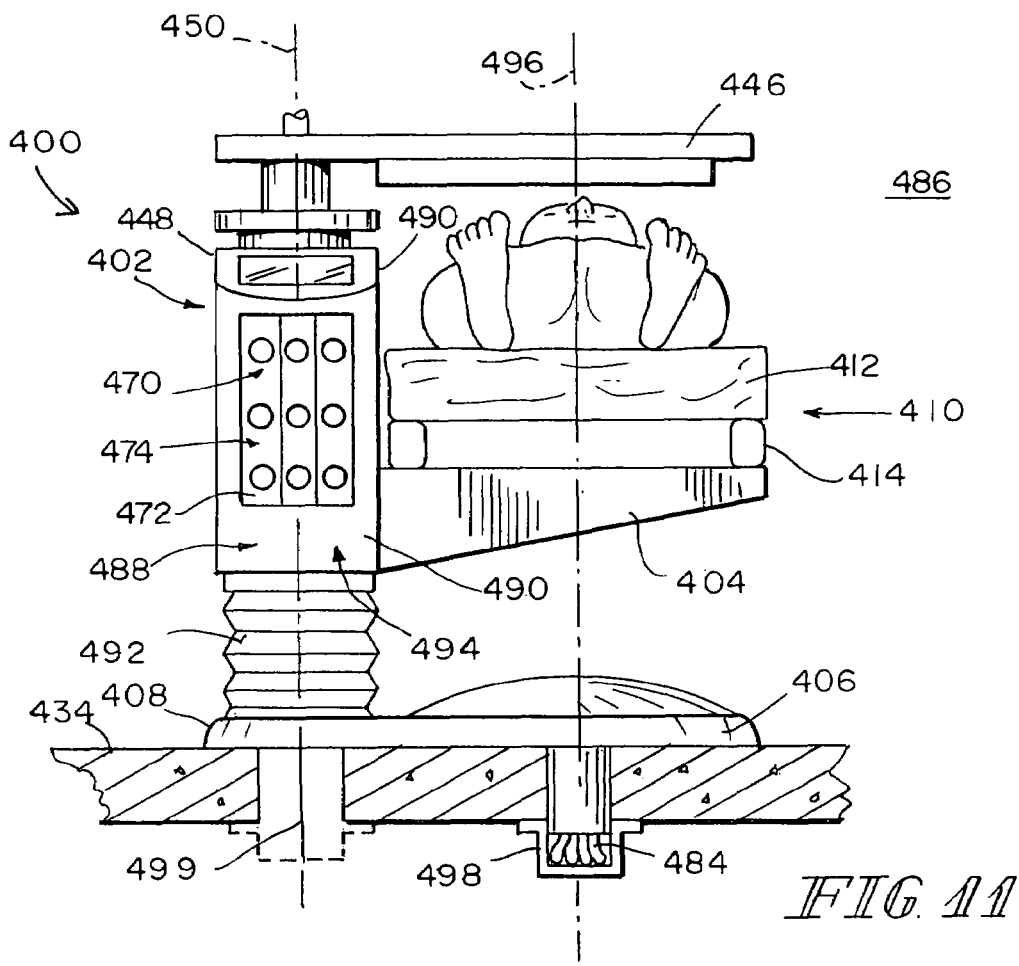
FIG. 11 is an end elevation view of the patient care module and the transfer top of FIG. 10, showing the table being vertically adjustable relative to the pedestal, the vertical axis about which the patient care module and transfer top pivots being generally "on center" with the patient, a preferred service channel (in solid) formed in the floor of the hospital room through which service delivery lines are routed to the patient care module, and an alternative service channel (in phantom) formed in the floor.
Figure 12:
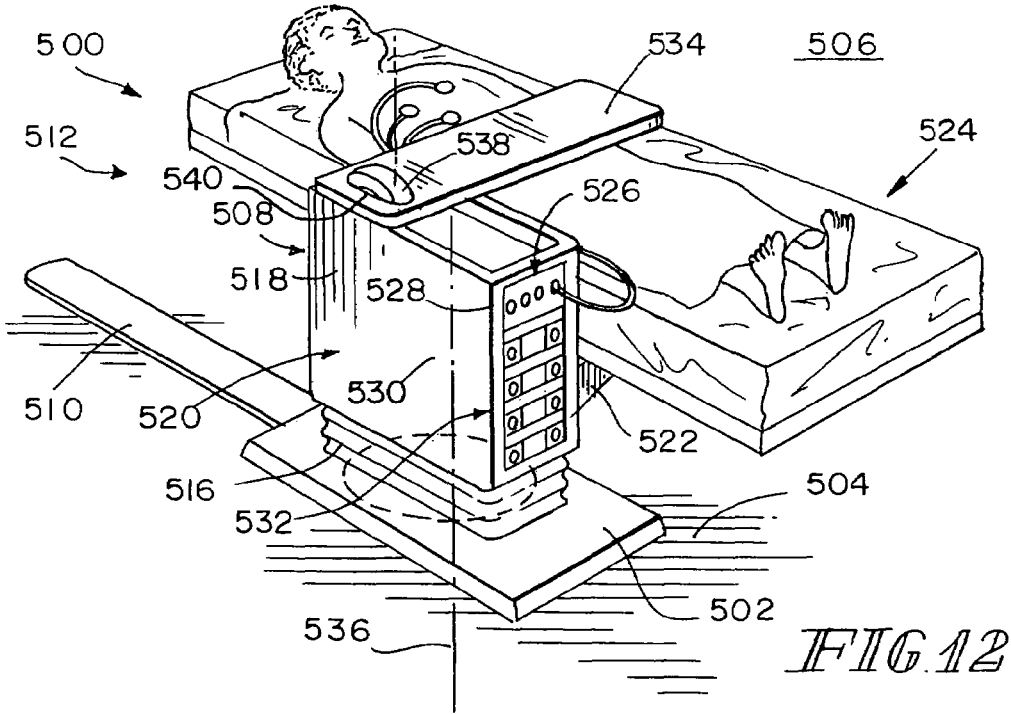
FIG. 12 is a perspective view of a first alternative patient care module, showing the first alternative patient care module including a rectangular base that rests upon a floor of a hospital room and a pedestal extending upwardly from the base, a supply conduit coupled to a head end of the base, the supply conduit containing portions of service delivery lines that are routed through the conduit to the first alternative patient care module, and a transfer top being supported by the patient care module above the floor.

According to the present disclosure, a floor-mounted patient care module 400 includes a pedestal 402 and a pair of lift arms 404 extending horizontally from the pedestal 402 as shown in FIG. 9. The patient care module 400 includes a base panel 406 (also referred to as a base) extending from a bottom portion 408 of the pedestal 402 beneath the lift arms 404 as shown in FIGS. 9 and 11. A transfer top 410 includes a mattress 412 and an articulating mattress support deck 414 that supports the mattress 412. The transfer top 410 is selectively couplable to the lift arms 404 of the patient care module 400 and to a transport base 420.

The transport base 420 includes a lower frame 422 having a cylindrical central hub 424 and six spokes 426 radiating substantially horizontally outwardly from the central hub 424 as shown in FIG. 9. The transport base 420 includes casters 428 coupled to the distal or outer ends of the spokes 426. The spokes 426 are grouped into a first set of three spokes 426 that extend generally forwardly from the hub 424 toward a head end 430 of the transport base 420 and a second set of three spokes 426 that extend generally rearwardly from the hub 424 toward a foot end 432 of the transport base 420. The casters 428 cooperate with the spokes 426 to elevate the central hub 424 above the floor 434. In addition, the casters 428 of the first set of three spokes 426 are spaced apart from the casters 428 of the second set of three spokes 426 by a sufficient distance that the base panel 406 is able to fit between the two groupings of casters 428 when the transport base 420 is moved to a position adjacent the lift arms 404.

The transport base 420 includes a vertical column 436 extending upwardly from the central hub 424 as shown in FIG. 9. An articulating frame 438 of the transport base 420 includes a center section 440 coupled to an upper end of the vertical column 436, a head-end section 442 coupled to a front edge of the center section 440, and a foot-end section 444 coupled to a rear edge of the center section 440. Each of the head-end and foot-end sections 442, 444 are pivotable relative to the center section 440 between respective horizontal positions, shown in FIG. 9 in solid, and respective vertical positions, shown in FIG. 9 in phantom. When the head-end and foot-end sections 442, 444 are in their respective vertical positions, the transport base 420 is configured for compact storage. The transfer top 410 is articulatable from a horizontal position, shown in FIG. 9, to a variety of positions, such as, for example, the position shown in FIG. 10 where a head-end section 416 of the transfer top 410 is raised and a foot-end section 418 of the transfer top 410 is slightly lowered to support a patient in a sitting-up or reclining position. When the transfer top 410 is coupled to the transport base 420, movement of the head-end and foot-end sections 442, 444 of the transport base 420 controls the movement of the head-end and foot-end sections 416, 418 of the transfer top 410, respectively.

The patient control module 400 includes a patient table 446 (also referred to as an overbed table) that is coupled to an upper portion 448 of the pedestal 402. The patient table 446 is pivotable relative to the pedestal 402 about a vertical axis 450 between a first position, shown in FIG. 10 in solid, extending laterally away from the pedestal 402 to overlie a patient's lap, and a second position, shown in FIG. 10 in phantom, extending laterally away from the pedestal on the side of the pedestal 402 opposite the transfer top 410. The upper portion 448 of the pedestal 402 is formed to include a storage recess 452 that is exposed when the patient table 446 is in the first and second positions. The patient table 446 includes an intermediate position between the first and second positions in which the table 446 covers the storage recess 452 as shown in FIG. 9. When the patient table 446 is in the first position, food for the patient may be placed on the table 446, and when the table 446 is in the second position, a caregiver may use the table 446 as a work surface. In some embodiments, the patient care module 400 includes drive mechanisms that are operable to change the elevation of the patient table 446 relative to the pedestal 402 as shown, for example, in FIG. 11 by a double-headed arrow 447, where the table 446 has been raised while in the first position overlying the patient.

Figure 10:
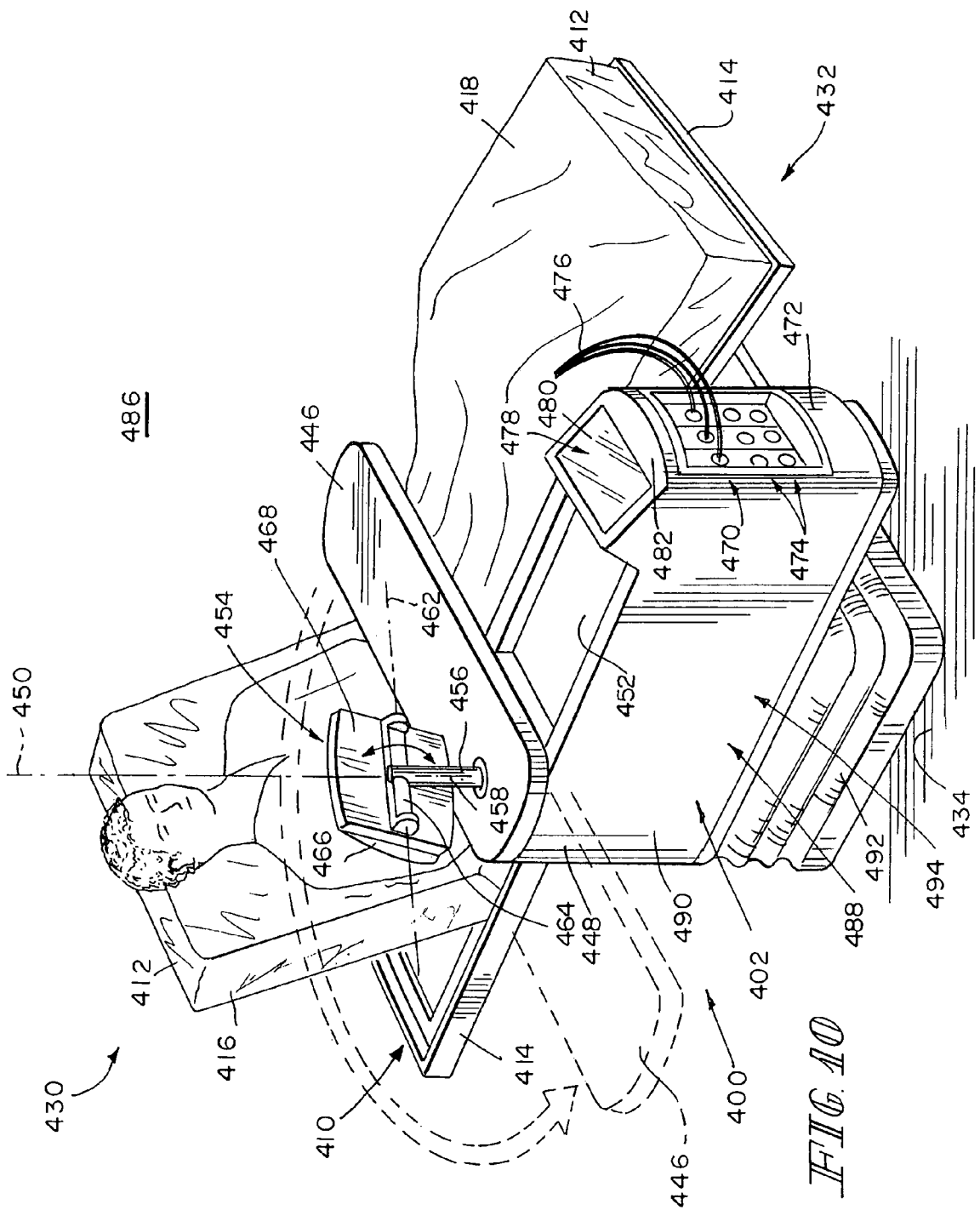
FIG. 10 is a perspective view of the patient care module and the transfer top of FIG. 9, showing a head section of the transfer top being raised to support a patient in a sitting-up position, an overbed table of the patient care module being pivotable relative to the pedestal about a vertical axis between a first position (in solid) extending laterally away from the pedestal to overlie the patient's lap and a second position (in phantom) extending laterally away from the pedestal on the side of the pedestal opposite the transfer top, a storage recess formed in a top surface of the pedestal being exposed when the table is in the first and second positions, the patient care module including a communication and control unit supported above the table, the communication and control unit having a phone and an interactive display accessible by the patient, and the patient care module including a plurality of service outlets and a caregiver control panel at an end of the pedestal inaccessible to the patient when the patient is lying on a mattress of the transfer top.

As shown in FIG. 10, the patient care module 400 includes a communication and control unit 454 supported above the patient table 446 by a T-shaped frame 456. A vertical portion 458 of the T-shaped frame 456 is pivotable about the vertical axis 450 independent of the pivoting of the patient table 446 about the vertical axis 450, and the communication and control unit 454 is pivotable about a horizontal axis 462 relative to a horizontal portion 464 of the T-shaped frame 456. The communication and control unit 454 includes a phone 466 having a handset and an interactive display 468 accessible by the patient supported on the transfer top 410.

A plurality of patient monitoring modules 470 are arranged in side-by-side relation along an upper portion of a vertical end face 472 of the pedestal 402 as shown in FIG. 10. In addition, a plurality of service outlets 474 are arranged on the vertical end face 472 beneath the patient monitoring modules 470. Each of the patient monitoring modules 470 receive patient data via patient data lines 476, the ends of which are coupled to a patient supported on the transfer top 410 to monitor the condition of the patient. Patient conditions to be monitored may include temperature, heart rate, blood oxygenation, respiration, brain activity, and the like.

A caregiver control panel 478 is accessible through an opening 480 formed in an inclined surface 482 of the pedestal 402. The control panel 478 is used to provide input parameters to and receive patient data from each of the patient monitoring modules 470. The control panel 478 is preferably a touch screen, although other types of control panels, such as those with knobs or buttons, may be included in the patient care module 400 in lieu of a touch screen. The service outlets 474 provide medical gases, vacuum, pressurized air, hydraulic fluid and power to various pieces of equipment that couple to the service outlets 474. The service outlets 474 receive the medical gases, vacuum, pressurized air, hydraulic fluid and power via service delivery lines 484 that are routed through the floor 434 of the hospital room 486 and into the interior region of the pedestal 402. The control panel 478, the service outlets 474, and the patient monitoring modules 470 are positioned on the pedestal 402 so as to be generally inaccessible to the patient when the patient is lying on the mattress 412 of the transfer top 410.

The patient care module 400 includes drive mechanisms 488 that operate to raise and lower the upper housing portion 490 of the pedestal 402 to which the lift arms 404 are coupled to change the elevation of the transfer top 410 and the patient supported thereon as indicated by a double-headed arrow 491. The pedestal 402 includes a lower bellows portion 492 that expands and contracts during raising and lowering of the upper housing portion 490. The patient care module 400 also includes drive mechanisms 494 that rotate the pedestal 402 and the transfer top 410 about a vertical axis 496 which is offset from the pedestal 402 and which is generally "on center" with the patient as shown in FIG. 11.

A preferred service channel 498, shown in FIG. 11 (in solid) is formed in the floor 434 of the hospital room. Service delivery lines 484 are routed to the patient care module 400 through the service channel 498 and enter an interior region of the base panel 406 through an opening formed in the underside of the base panel 406 in the vicinity of the vertical axis 496. Alternatively, a service channel 499, shown in FIG. 11 (in phantom) may be formed in the floor 434 of the hospital room beneath the pedestal 402.

According to this disclosure, a first alternative floor-mounted patient care module 500 includes a rectangular base plate 502 (also referred to as a base) that rests upon a floor 504 of a hospital room 506 and a pedestal 508 extending upwardly from the base 502 as shown in FIGS. 12-15. A supply conduit 510 is coupled to a head end 512 of the base 502. The supply conduit 510 contains portions of service delivery lines 514, shown in FIG. 13, that are routed through the supply conduit 510 to the patient care module 500. The pedestal 508 includes a lower housing 516 extending upwardly from the base 502 and an upper housing 518 that is coupled to the lower housing 516 for vertical telescoping movement. The patient care module 500 includes drive mechanisms 520 that operate to raise and lower the upper housing 518 relative to the lower housing 516. A pair of lift arms 522 are coupled to the upper housing 518 to raise and lower therewith. The lift arms 522 are configured to support a transfer top 524 as shown in FIGS. 12-15. The transfer top 524 and the operation thereof is substantially similar to the transfer top 410 of FIGS. 9-11.

Figure 13:
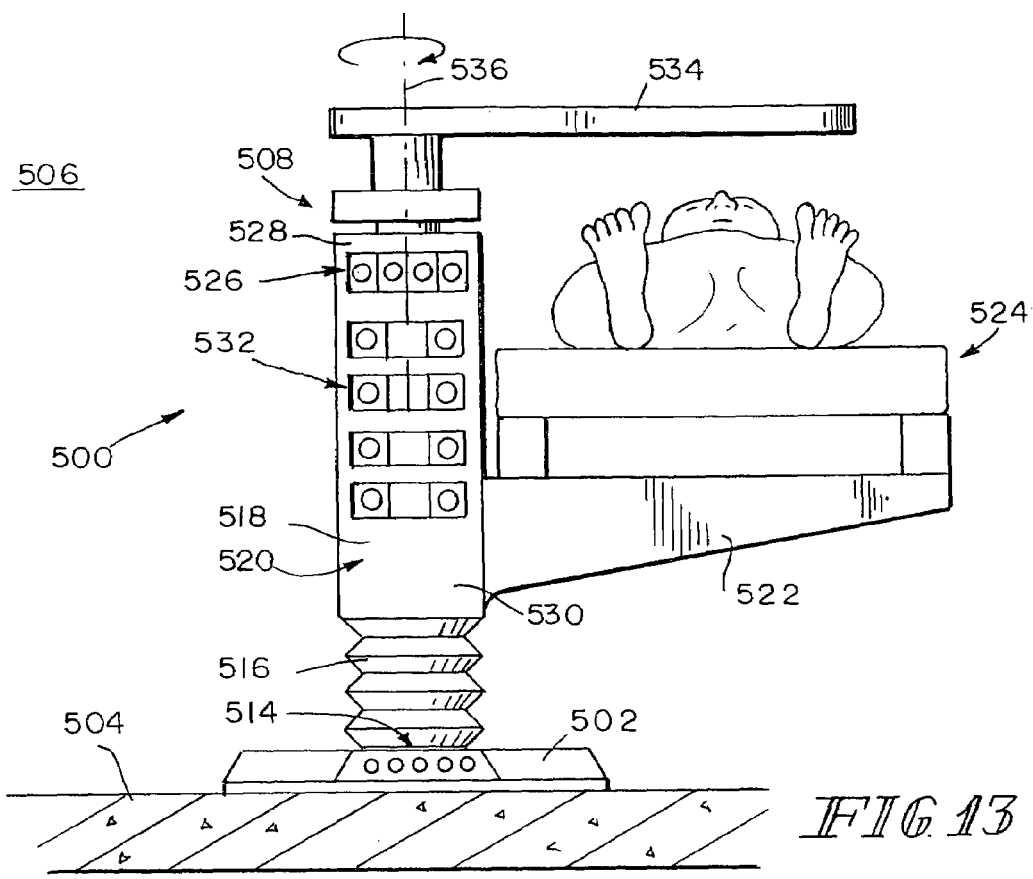
FIG. 13 is an end elevation view of the first alternative patient care module and transfer top of FIG. 12, showing the first alternative patient care module including a plurality of service outlets along an end face of the pedestal and an overbed table that is rotatable relative to the pedestal about a vertical axis to a position overlying the patient supported by the transfer top.

A plurality of patient monitoring modules 526 are arranged in side-by-side relation along an upper portion 528 of a vertical end face 530 of the pedestal 508 as shown best in FIG. 13. In addition, a plurality of service outlets 532 are arranged on the end face 530 beneath the patient monitoring modules 526. The service delivery lines 514 are coupled to the service outlets 532 in the interior region of the upper housing 518 of the pedestal 508. The patient care module 500 includes an overbed or patient table 534 that is rotatable relative to the pedestal 508 about a vertical axis 536 between a first position, shown in FIG. 14, in which the patient table 534 overlies the entire upper surface of the pedestal 508 and a second position, shown in FIGS. 12, 13 and 15, in which the patient table 534 overlies the patient supported on the transfer top 524. The patient care module 500 includes a telephone 538, shown in FIG. 15, that is situated in a phone-receiving recess 540 formed in the patient table 534.

Figure 14:
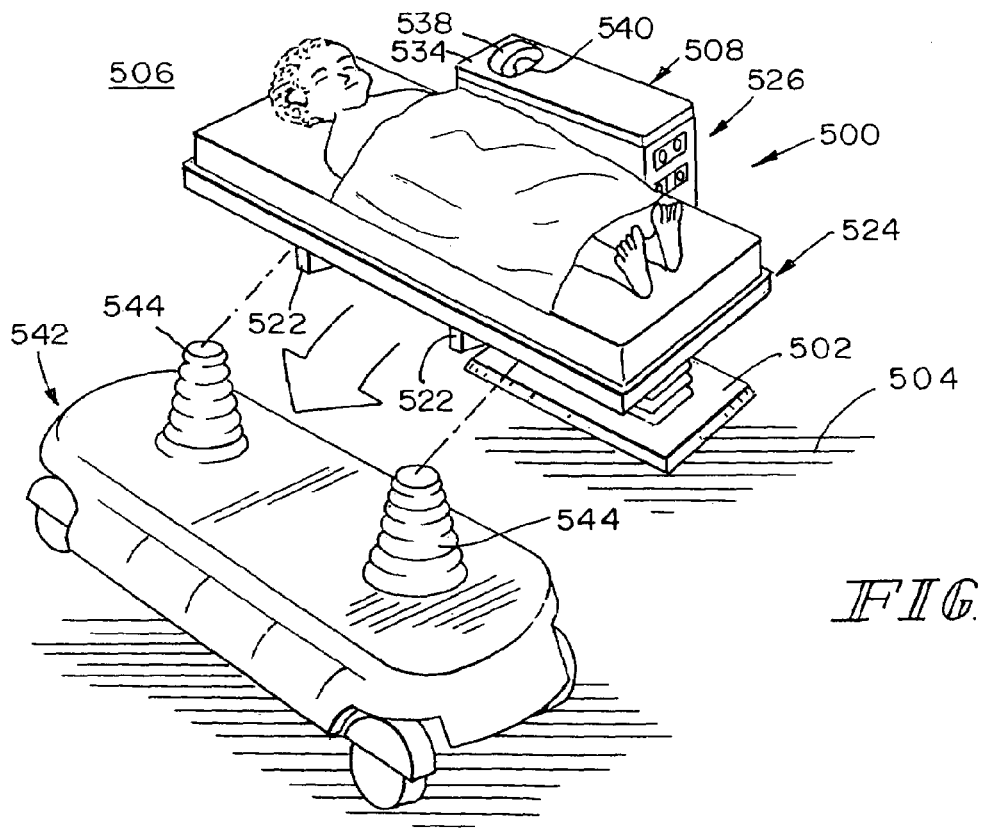
FIG. 14 is a perspective view of the first alternative patient care module and transfer top of FIG. 13, showing the transfer top being moved from the lift arms of the first alternative patient care module to a stretcher base in the direction of the arrow.
Figure 15:
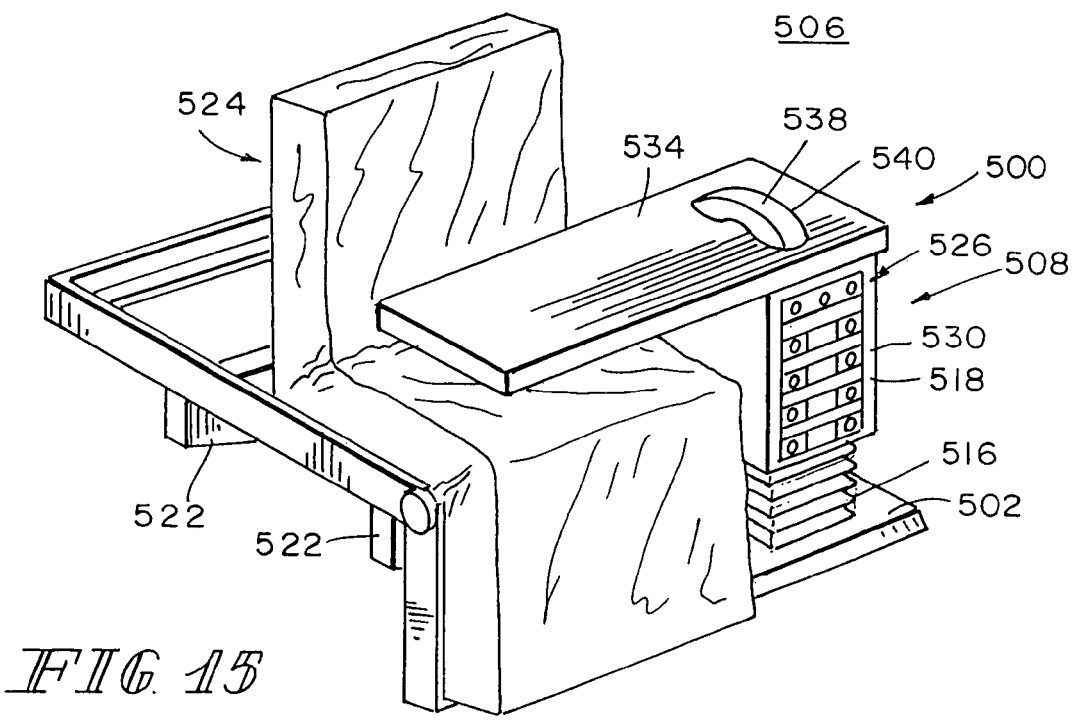
FIG. 15 is a perspective view similar to FIG. 14, showing the transfer top moved to a chair position having a head section of the transfer top extending upwardly from a seat section of the transfer top and having a foot section of the transfer top extending downwardly from the seat section, and showing the alternative patient care module including a telephone coupled to the overbed table.

The transfer top 524 is transferable between the patient care module 500 and a stretcher base 542 as shown in FIG. 14. The stretcher base 542 includes a pair of spaced-apart upstanding lift assemblies 544 to which the transfer top 524 couples when being transported by the stretcher base 542. The patient care module 500 includes a first set of coupling mechanisms that secure the transfer top 524 to the lift arms 522. The stretcher base 542 includes a second set of coupling mechanisms that secure the transfer top 524 to the lift assemblies 544. In some embodiments, the transfer top 524 includes coupling mechanisms that are configured to secure the transfer top 524 to the lift arms 522 and to the lift assemblies 544. When coupled to the lift arms 522, the transfer top 524 is movable between a horizontal table configuration, shown in FIGS. 12-14, and a chair configuration, shown in FIG. 15.

Figure 16:
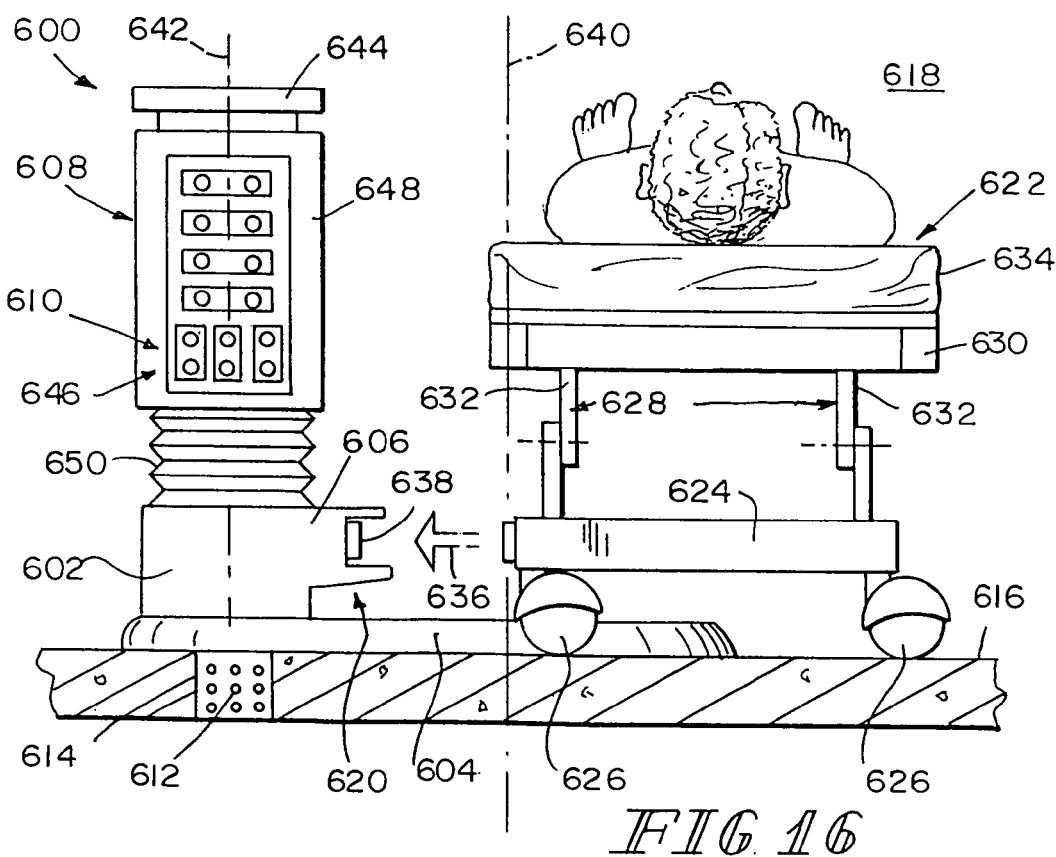
FIG. 16 is an end elevation view of a hospital bed and a second alternative patient care module, showing the hospital bed having a base frame that is movable in the direction of the horizontal arrow to dock to a lower portion of a pedestal of the second alternative patient care module, and showing the second alternative patient care module and the hospital bed being pivotable about a vertical axis once the hospital bed docks to the lower portion of the pedestal.

Referring now to FIG. 16, a second alternative floor-mounted patient care module 600 includes a base 602 having a floor-engaging portion 604 and a docking port 606. The patient care module 600 further includes a pedestal 608 and a set of service outlets 610 coupled to the pedestal 608. Service delivery lines 612 are routed from channels 614 formed in a floor 616 of a hospital 618, through the base 602, and through the pedestal 608. Ends of the service delivery lines 612 are coupled to the back sides of the service outlets 610 in the interior region of the pedestal 608 in a manner well known to those skilled in the art.

The docking port 606 of the base 602 includes a gripper or coupler 620 as shown in FIG. 16. A hospital bed 622 includes a base frame 624, a set of casters 626 coupled to the base frame 624 and extending downwardly therefrom, a set of lift linkages 628 coupled to the base frame 624 and extending upwardly therefrom, a patient support deck 630 coupled to the upper ends 632 of the lift linkages 628, and a mattress 634 supported by the patient support deck 630. The hospital bed 622 is movable in the direction indicated by a horizontal arrow 636 to dock to the docking port 606 of the base 602 of the patient care module 600. In preferred embodiments, the coupler 620 includes elements, such as latches or clutches, that automatically grasp onto the base frame 624 of the hospital bed 622 upon entry of a portion of the base frame 624 into a frame receiving space 638 of the coupler 620. Suitable release mechanisms are provided to actuate the coupler 620 to release the base frame 624 of the hospital bed 622 when desired.

When the hospital bed 622 is docked to the patient care module 600, the patient care module 600 and the hospital bed 622 are pivotable as a unit about a vertical axis 640 that is offset from the pedestal 608. In some embodiments, when the hospital bed 622 is docked to the patient care module 600, the patient care module 600 and the hospital bed 622 are pivotable as a unit about a vertical axis 642 that passes through the pedestal 608. The patient care module 600 includes an overbed or patient table 644 similar to the patient table 446 of FIGS. 9-11. The patient care module 600 also includes drive mechanisms 646 that operate to raise and lower a housing portion 648 of the pedestal 608 relative to the base 602. The pedestal 608 includes a bellows portion 650 that expands and contracts during raising and lowering, respectively, of the housing portion 648.

Figure 17:
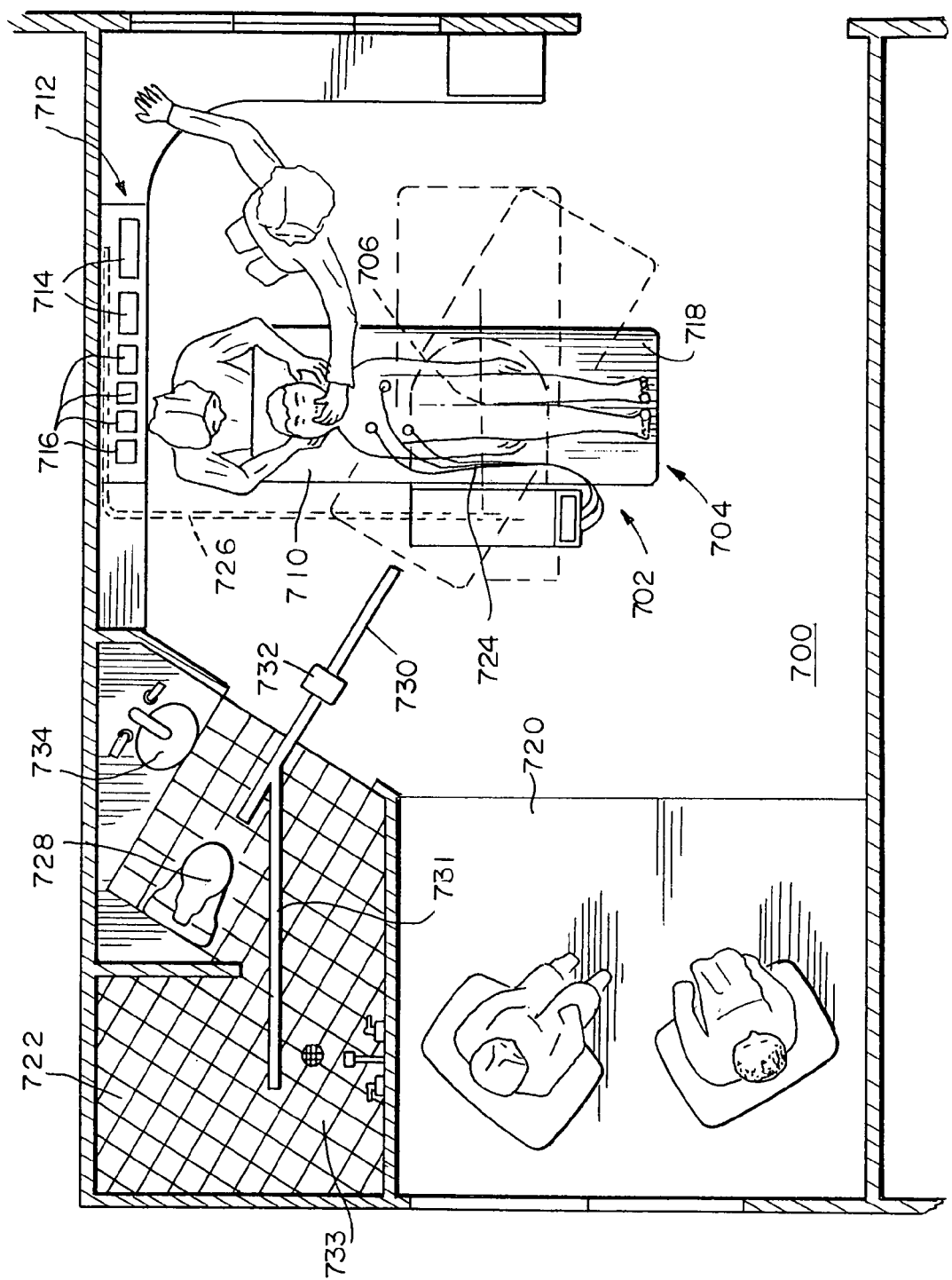
FIG. 17 is a top plan view of a hospital room in which the patient care module of FIGS. 9-11 is included, showing the transfer top and patient care module being movable between a first position (in solid) having a head end of the transfer top facing toward a headwall in which medical data monitors and gas supplies are housed, a second position (in phantom) having a foot end of the transfer top facing toward a visitor area of the hospital room, and a third position (in phantom) having the foot end of the transfer top facing toward a bathroom area of the hospital room, a ceiling support track extending from the transfer top to a toilet included in the bathroom area, and a patient support device attached to the ceiling support track and used by a patient to ambulate to the bathroom area when the transfer top is moved to the third position and articulated to a chair position which facilitates patient egress from the transfer top.

FIG. 17 is a top plan view of a hospital room 700 in which a floor-mounted patient care module 702 and a transfer top 704 are included. Illustratively, the patient care module 702 and the transfer top 704 are of the type shown in FIGS. 9-11. The transfer top 704 and the patient care module 702 are rotatable in the hospital room 700 about a vertical axis 706 between a plurality of positions, including a first position (in solid) having a head end 710 of the transfer top 704 facing toward a headwall 712 in which medical data monitors 714 and various gas supply components 716 are housed, a second position (in phantom) having a foot end 718 of the transfer top 704 facing toward a visitor area 720 of the hospital room 700, and a third position (in phantom) having the foot end 718 of the transfer top 704 facing toward a bathroom area 722 of the hospital room 700. As the patient care module 702 and the transfer top 704 are moved between positions, patient data lines 724 maintain their orientations relative to the patient lying on the transfer top 704 and relative to the patient care module 702. Thus, because the transfer top 704 and the patient care module 702 rotate together about the vertical axis 706, unwanted pulling, entanglement, and disconnection of patient data lines 724 is avoided.

A ceiling support track 730 extends between the transfer top 704 and a toilet 728 included in the bathroom area 722. A patient support device 732, such as a harness, a handle bar, or a seat, hangs from the ceiling support track 730. The patient support device 732 is used by the patient to ambulate to the bathroom area 722 after the transfer top 704 is first moved to the third position having the foot end 718 facing toward the bathroom area 722 and then moved to a chair position allowing patient egress from the transfer top 704. A sink 734 is located in bathroom area 722 in close proximity to the toilet 728. Therefore, the patient has access both to the toilet 728 and the sink 734 while still being supported by the patient support device 732 hanging from the ceiling support track 730. A secondary track 731 extends from the ceiling support track 730 to a shower portion 733 of the bathroom area 722. In some embodiments, an overhead track supported by a framework assembly is used as an alternative to the ceiling support track. Tracks coupled to a ceiling or coupled to a framework assembly and patient support devices used with these tracks are well known in the hospital art.

Figure 18:
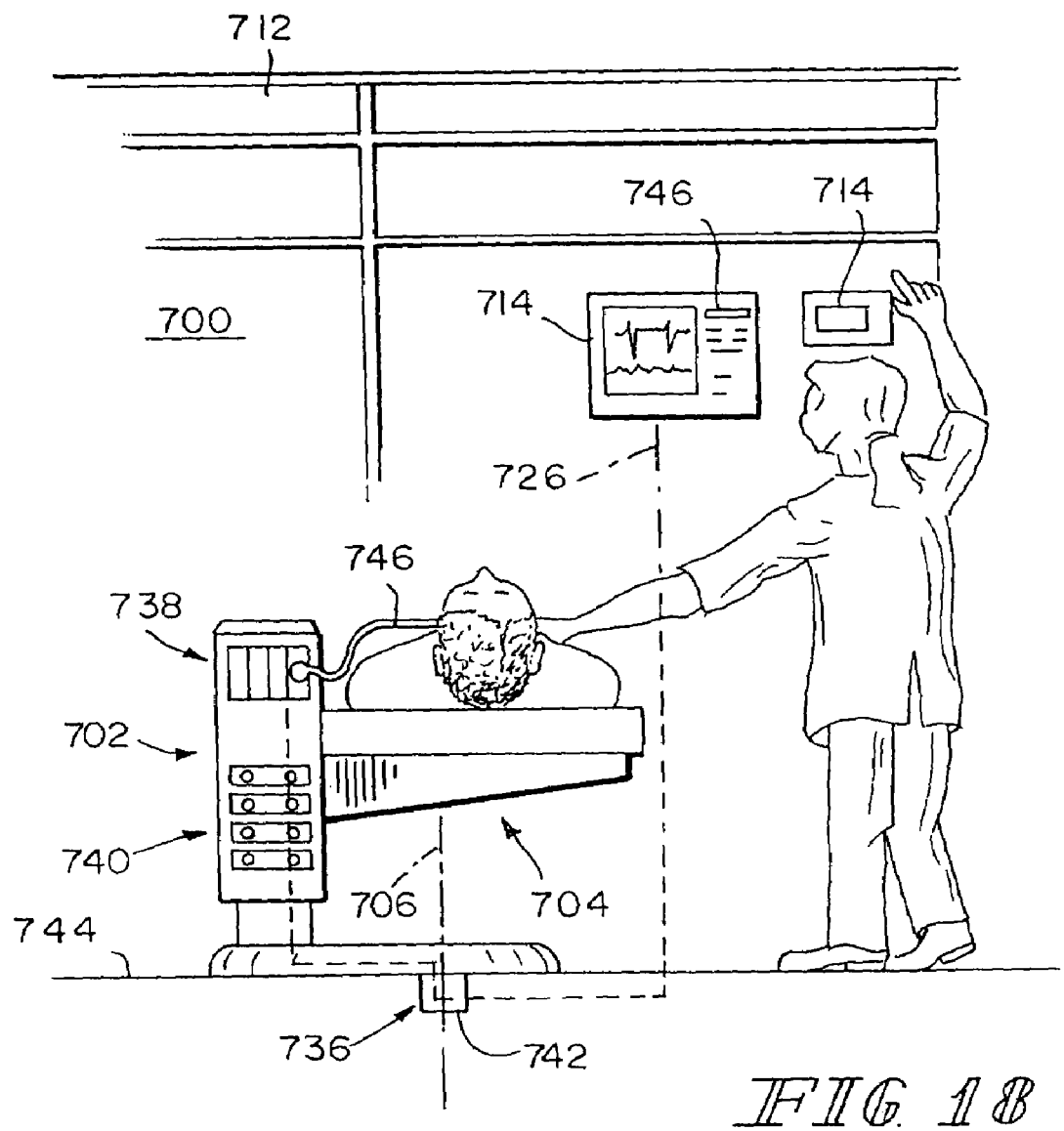
FIG. 18 is an end elevation view of the patient care module and transfer top of FIG. 17, showing a caregiver viewing one of the medical data monitors housed in the headwall, data from the patient being transmitted to the patient care module via a first data line that extends from the patient to one of the patient monitoring modules included in the pedestal, and the medical data monitor receiving data from the pedestal via a second data line (in phantom) that is routed to the medical data monitor through the patient care module, through the service channel formed in the floor of the hospital room, and behind a front panel of the headwall.

Service and data lines 736 are illustrated diagrammatically in FIGS. 17 and 18 as a single dashed line. However, it will be appreciated that multiple services and data lines 736 are routed from the patient care module 702 to the associated medical equipment, such as medical data monitors 714 and gas supply components 716. The service and data lines 736 are routed from respective patient monitoring modules 738 and service outlets 740 through the interior regions of the patient care module 702, through the service channel 742 formed in the floor 744 of the hospital room 700, and through interior regions of the headwall 712 as shown in FIGS. 17 and 18. Signals generated by sensors coupled to the patient are transmitted to the patient monitoring modules 738 via patient data lines 724, and the medical data monitors 714 receive these signals either in raw form or after processing by the patient monitoring modules 738, via the data lines 736.

The medical data monitors 714 housed in the headwall 712 include control panels 746, shown in FIG. 18, that are used to control the operation of the medical data monitors 714. The control panels 746 may be used by a caregiver, for example, to select which of the signals received from the patient monitoring modules 738 are to be displayed on the associated monitor 714 or to adjust the manner in which a signal from a particular patient monitoring module 738 is to be displayed. The gas supply components 716 may include manifolds, valves, pressure regulators, pressure sensors, alarms and the like. It is within the scope of this disclosure for other types of medical equipment to be included in the headwall 712 and to be coupled to the patient care module 702 via lines 736. Because lines 736 are hidden from view due to routing through the patient care module 702, the floor 744 of the hospital room 700, and the headwall 712, the amount of clutter in the room 700 is kept to a minimum even though the patient is hooked up to numerous pieces of medical equipment.

According to the present disclosure, a column-mounted docking station 800 includes a vertical column 802, a docking port 804 coupled to the column 802 near a lower end 806 thereof, a communication-and-control unit 810 coupled to the column 802 above the docking port 804 and an overbed or patient table 812 coupled to the communication-and-control unit 810 as shown in FIGS. 19 and 20. The vertical column 802, the docking port 804, the communication-and-control unit 810, and the patient table 812 are rotatable together about a vertical axis 814 defined by the column 802. The upper end 808 of the column 802 is coupled to a ceiling 816 of a hospital room 818 and the lower end 806 of the column 802 is coupled to a floor 820 of the hospital room 818 as shown in FIG. 20. Suitable couplings are provided to connect the column 802 to the ceiling 816 and to the floor 820 and to permit rotation of the column 802 about the vertical axis 814.

A proximal end 822 of the docking port 804 is coupled to the vertical column 802 and a distal end 824 of the docking port 804 is formed to include a channel or frame-receiving space 826 as shown in FIG. 19. Thus, the docking port 804 extends horizontally from the column 802 in a cantilevered fashion. A hospital bed 828 includes a base frame 830, a set of casters 832 coupled to the base frame 830 and extending downwardly therefrom, a set of lift linkages 834 coupled to the base frame 830 and extending upwardly therefrom, a patient support deck 836 and a mattress 838 supported by the deck 836. A side frame member 840 of the base frame 830 of the hospital bed 828 is receivable in the frame-receiving space 826 to dock the bed 828 to the docking station 800. The docking port 804 includes one or more grippers or couplers 842, such as, for example, latches or clutches, that automatically grasp onto the base frame 830 or that interface with suitable elements on the base frame 830 to lock the bed 828 to the docking station 800 upon entry of the side frame member 840 of the base frame 830 into the frame-receiving space 826. Suitable release mechanisms are provided to actuate the couplers 842 to release the base frame 830 of the hospital bed 828 from the docking station 800 when desired. When the hospital bed 828 is docked to the docking station 800, the bed 828 is rotatable with the docking station 800 about the vertical axis 814.

The docking station 800 includes one or more service outlets 844 coupled to a vertical end face 846 of the docking port 804. The column 802 includes one or more internal passages that communicate with an interior region of the docking port 804. Service delivery lines 847 are routed either downwardly from the ceiling 816 or upwardly from the floor 820, through the internal passages of the column 802, and through the interior region of the docking port 804. Each service delivery line 847 terminates at a respective service outlet 844. The service delivery lines 847 include, for example, AC power lines, DC power lines, video lines, audio lines, data transmission lines, communication lines, and the like. It is within the scope of this disclosure for other services, such as medical gases, vacuum, hydraulic fluid, and pressurized air to be supplied by the service delivery lines 847 to associated service outlets 844 mounted on the docking port 804. The base frame 830 of the hospital bed 828 includes service connectors that mate with the service outlets 844 so that services are provided to the bed 828 and so that communication links are established when the bed 828 docks to the docking station 802.

A lower portion 848 of the communication-and-control unit 810 is formed to include an elongated, horizontal slot 850 as shown in FIG. 19. A patient table 812 is coupled to the communication-and-control unit 810 for pivoting movement between a storage position in which the table 812 is situated within the slot 850 and a patient-use position in which a majority of the table 812 is positioned to lie outside of the slot 850. In alternative embodiments, the patient table 812 translates into and out of the horizontal slot 850. When in the patient-use position, the table 812 extends horizontally outwardly from the communication-and-control unit 810. In the illustrative embodiment, the patient table 812 pivots through 90 degrees when moving between the storage position and the patient-use position. The patient table 812 is also able to pivot by 180 degrees from the patient-use position to a caregiver-use position in which the table 812 extends horizontally from the communication-and-control unit 810 in a direction away from the hospital bed 828.

In some embodiments, the patient table 812 includes multiple segments that fold, telescope, or otherwise move relative to each other so that the table 812 can be manipulated into a compact configuration for storage. In addition, the docking station 800 includes suitable locking mechanisms to lock the patient table 812 in the storage, patient-use and caregiver-use positions. The docking station 800 includes drive mechanisms 854 that operate to change the vertical position of the communication-and-control unit 810 and the table 812 along the column 802 as indicated by a double-headed dashed arrow 856 shown in FIG. 20.

The communication-and-control unit 810 is formed to include a cavity 858 in which various pieces of communication-and-control devices are located. For example, a control panel 860 is coupled to a recessed vertical wall 862 of the communication-and-control unit 810, a display screen 864 is coupled to a side wall 866 of the communication-and-control unit 810, and a telephone handset 868 rests upon a bottom wall 870 of the communication-and-control unit 810. The control panel 860 includes user inputs to control, for example, room lighting, room temperature, television functions, nurse call functions, and the like. The display screen 864 displays various images such as, for example, television images, internet images, educational information, patient schedule, patient billing information, and video conferencing images. The telephone handset 868 is used in a conventional manner for placing and receiving of phone calls.

Although the several inventions have been described in detail with reference to certain preferred embodiments, variations and modifications exist within the scope and spirit of the invention as described and defined in the following claims.

The invention claimed is:

1. A docking station for use in a hospital having a room wall, the docking station comprising:
a transfer top,
at least one support rail extending away from the room wall, and adapted to support the transfer top, and
a support leg,
wherein, the support leg is coupled to a distal end of the support rail and selectively extends downwardly to engage a floor of the hospital.

2. The docking station of claim 1, wherein the at least one support rail includes a pair of support rails extending away from the room wall, wherein the pair of support rails are adapted to receive and support the transfer top, and wherein the support leg includes a pair of support legs each coupled to a distal end of one of the pair of support rails.

3. The docking station of claim 2 including a pair of siderails, each siderail being coupled to a respective support rail.

4. The docking station of claim 2, wherein the transfer top includes a head section, a seat section and a foot section, wherein the head section of the transfer top is configured to pivot upwardly to a raised position, and wherein the foot section of the transfer top is configured to pivot downwardly to a lowered position.

5. The docking station of claim 4, wherein the seat section of the transfer top is configured to move horizontally along the support rails toward a foot end of the support rails as the head section of the transfer top is pivoted upwardly to the raised position and the foot section of the transfer top is pivoted downwardly to the lowered position, and wherein the siderails are configured to move horizontally with the seat section toward the foot end of the support rails.

6. The docking station of claim 2 including a drive, wherein the transfer top and the support rails are configured to move downwardly by the drive to a lowered position.

7. The docking station of claim 6, wherein a foot end section of one of the siderails is configured to pivot laterally outwardly relative to a head end section of the said siderail to allow patient egress from a side of the transfer top.

8. An apparatus for use in a hospital having a room wall, the apparatus comprising:
- a transport trolley,
- a docking station coupled to the room wall, and
- a transfer top having a retractable leg that pivots relative to the transfer top between a use position extending downwardly from the transfer top to engage a floor and a storage position spaced apart from the floor,
- wherein the docking station includes a lift mechanism and a lift arm extending horizontally in a cantilevered fashion from the lift mechanism,
- wherein the lift arm is adapted to support the transfer top,
- wherein the transfer top is transferable between the lift arm and the transport trolley, and
- wherein the lift mechanism is operable to raise and lower the lift arm and the transfer top.

9. The apparatus of claim 8, wherein the transport trolley is arranged to move to a position beneath the transfer top so that the transfer top can be decoupled from the docking station and coupled to the transport trolley so that the transfer top can be transported away from the docking station by the transport trolley.

10. The apparatus of claim 8, wherein the transfer trolley engages the retractable leg and moves the retractable leg from the use position to the storage position when the transport trolley is moved to a position beneath the transfer top.

11. The apparatus of claim 8, wherein the transfer top includes a mattress and a mattress support deck beneath the mattress, wherein the mattress support deck is coupled to the lift arm to raise and lower therewith, and wherein the retractable leg extends horizontally adjacent an undersurface of the mattress support deck in the storage position.

12. An apparatus for use in a hospital having a room wall, the apparatus comprising:
- a lift arm extending horizontally in a cantilevered fashion away from the room wall,
- a bolster coupled to the lift arm, the bolster being configured to define a mattress-receiving space, and
- a mobile platform having a movable base and a mattress carried by the movable base, the mobile platform being movable to a position where the mattress is received in the mattress-receiving space,
- wherein the bolster includes an upper surface that cooperates with an upper surface of the mattress to increase the amount of surface area available to support a patient when the mattress is received in the mattress-receiving space.

\* \* \* \* \*